US008636011B2

(12) United States Patent
Strickland et al.

(10) Patent No.: US 8,636,011 B2
(45) Date of Patent: Jan. 28, 2014

(54) TOBACCO COMPOSITIONS

(75) Inventors: James A Strickland, Goodlettsville, TN (US); Frank S. Atchley, Nashville, TN (US); James M. Rossman, Tampa, FL (US); Armand J. Desmarais, Inverness, FL (US); Scott A. Williams, Greenbrier, TN (US); Tod J. Miller, Smyrna, TN (US); Cherne W. Johnson, Antioch, TN (US); Vernie A. Due, Kansas City, MO (US)

(73) Assignee: U.S. Smokeless Tobacco Company LLC, Richmond, VA (US)

( * ) Notice: Subject to any disclaimer, the term of this patent is extended or adjusted under 35 U.S.C. 154(b) by 145 days.

(21) Appl. No.: 12/345,012

(22) Filed: Dec. 29, 2008
(Under 37 CFR 1.47)

(65) Prior Publication Data
US 2009/0133703 A1 May 28, 2009

Related U.S. Application Data

(62) Division of application No. 10/982,248, filed on Nov. 5, 2004, now Pat. No. 8,469,036.

(60) Provisional application No. 60/518,352, filed on Nov. 7, 2003, provisional application No. 60/603,888, filed on Aug. 23, 2004.

(51) Int. Cl.
*A24B 15/00* (2006.01)

(52) U.S. Cl.
USPC .......................................................... 131/352

(58) Field of Classification Search
None
See application file for complete search history.

(56) References Cited

U.S. PATENT DOCUMENTS

| | | | |
|---|---|---|---|
| 1,376,586 A | 5/1921 | Schwartz | |
| 2,734,510 A | 2/1956 | Hungerford et al. | |
| 2,770,241 A | 11/1956 | Winkler | |
| 3,046,993 A | 7/1962 | Rich | |
| 3,067,068 A | 12/1962 | Finberg | |
| 3,098,492 A * | 7/1963 | Wurzburg et al. | 131/375 |
| 3,151,996 A | 10/1964 | Desmarais | |
| 3,166,078 A | 1/1965 | Parmele et al. | |
| 3,240,214 A | 3/1966 | Bayley et al. | |
| 3,292,635 A | 12/1966 | Kolodny | |
| 3,313,305 A | 4/1967 | Noznick et al. | |
| 3,435,027 A | 3/1969 | Desmarais et al. | |
| 3,455,714 A | 7/1969 | Bishop et al. | |
| 3,470,883 A | 10/1969 | Shepherd et al. | |
| 3,483,148 A | 12/1969 | Desmarais | |
| 3,625,225 A | 12/1971 | Halter | |
| 3,835,074 A | 9/1974 | Desmarais | |
| 3,857,972 A | 12/1974 | Evers et al. | |
| 3,891,582 A | 6/1975 | Desmarais | |
| 3,942,537 A | 3/1976 | Evers et al. | |
| 3,949,762 A | 4/1976 | West et al. | |
| 3,951,155 A | 4/1976 | Prouse et al. | |
| 3,968,804 A | 7/1976 | Kelly et al. | |
| 4,014,349 A | 3/1977 | Morman et al. | |
| 4,014,541 A | 3/1977 | Desmarais | |
| 4,065,319 A | 12/1977 | Desmarais | |
| 4,136,145 A | 1/1979 | Fuchs et al. | |
| 4,136,162 A | 1/1979 | Fuchs et al. | |
| 4,142,535 A | 3/1979 | Perkins et al. | |
| 4,305,502 A | 12/1981 | Gregory et al. | |
| 4,325,391 A | 4/1982 | Schmidt | |
| 4,371,516 A | 2/1983 | Gregory et al. | |
| 4,501,617 A | 2/1985 | Desmarais | |
| 4,513,756 A | 4/1985 | Pittman et al. | |
| 4,515,769 A | 5/1985 | Merritt et al. | |
| 4,517,173 A | 5/1985 | Kizawa et al. | |
| 4,558,079 A | 12/1985 | Desmarais | |
| 4,596,259 A | 6/1986 | White et al. | |
| 4,606,357 A | 8/1986 | Dusek et al. | |
| 4,624,269 A | 11/1986 | Story et al. | |
| 4,661,359 A | 4/1987 | Seaborne et al. | |
| 4,683,256 A | 7/1987 | Porter et al. | |
| 4,706,692 A | 11/1987 | Gellatly | |
| 4,713,243 A | 12/1987 | Schiraldi et al. | |
| 4,724,850 A | 2/1988 | Graves, Jr. | |
| 4,725,441 A | 2/1988 | Porter et al. | |
| 4,754,767 A | 7/1988 | Graves, Jr. | |
| 4,764,378 A | 8/1988 | Keith et al. | |
| 4,795,641 A | 1/1989 | Kashdan | |
| 4,806,356 A | 2/1989 | Shaw | |
| 4,807,648 A | 2/1989 | Breckwoldt | |

(Continued)

FOREIGN PATENT DOCUMENTS

| | | |
|---|---|---|
| CN | 1037317 C | 2/1998 |
| CN | 1354656 A | 6/2002 |

(Continued)

OTHER PUBLICATIONS

Office Action Taiwan Application No. 093133982, dated Apr. 2011, 9 pages.
Office Action/Notice of Reasons for Rejection Japanese Patent Application No. 2006-539648, dated Jan. 6, 2011, 30 pages.
Seville et al., "Agglomeration of Tobacco Dust", Jan. 21, 1985 , University of Surrey/British American Tobacco, p. 1, "Background", accessed via http://legacy.library.ucsf.edu/tid/ogd61a99 on Feb. 3, 2012.
United States Tobacco Co. Makes First Change in 422 years of Snuff, Western Tobacco Journal, Apr. 14, 1960.
U.S. Smokeless Tobacco, "Copenhagen Snuff Final Casing Procedure," Oct. 1974, [retrieved on May 17, 2012] Retrieved from the Internet:<URL: http://legacylibrary.ucsf.edu/tid/yos71b00>; 1 page.
European Search Report for EP Application No. 04800749.6, dated Aug. 3, 2012, 6 pages.
"A Film Worth Eating?" *Food Research & Development*, Aug. 1994, 1:1.
"Corn Pays a Chemical Dividend," *Chemical Week*, 1964, pp. 63-64.
"Curdlan—New Polysaccharide Offers Gel Options," *Food Formulating*, 1996, 2(10):17.

(Continued)

*Primary Examiner* — Michael J Felton
(74) *Attorney, Agent, or Firm* — Fish & Richardson P.C.

(57) ABSTRACT

The invention features tobacco compositions and methods of their use and manufacture. Compositions of the invention may be based on a variety of technologies. Technologies include films, tabs, shaped parts, gels, consumable units, insoluble matrices, and hollow shapes. In addition to tobacco, compositions may also contain flavors, colors, and other additives as described herein. Compositions may also be orally disintegrable. Exemplary compositions and methods of their manufacture are described herein.

21 Claims, No Drawings

(56) References Cited

U.S. PATENT DOCUMENTS

| | | | |
|---|---|---|---|
| 4,821,745 | A | 4/1989 | Rosen et al. |
| 4,823,817 | A | 4/1989 | Luke |
| 4,824,681 | A | 4/1989 | Schobel et al. |
| 4,828,841 | A | 5/1989 | Porter et al. |
| 4,828,843 | A | 5/1989 | Pich et al. |
| 4,849,246 | A | 7/1989 | Schmidt |
| 4,874,000 | A * | 10/1989 | Tamol et al. ............ 131/375 |
| 4,880,018 | A | 11/1989 | Graves, Jr. et al. |
| 4,907,605 | A | 3/1990 | Ray et al. |
| 4,907,606 | A | 3/1990 | Lilja et al. |
| 4,911,934 | A | 3/1990 | Yang et al. |
| 4,917,161 | A | 4/1990 | Townend |
| 4,917,924 | A | 4/1990 | Huang et al. |
| 4,967,773 | A | 11/1990 | Shaw |
| 4,971,079 | A | 11/1990 | Talapin et al. |
| 4,972,855 | A | 11/1990 | Kuriyama et al. |
| 4,977,908 | A | 12/1990 | Luke |
| 4,981,522 | A * | 1/1991 | Nichols et al. ............ 131/274 |
| 4,985,260 | A | 1/1991 | Niaura et al. |
| 4,987,906 | A | 1/1991 | Young et al. |
| 5,019,403 | A | 5/1991 | Krochta |
| 5,024,701 | A | 6/1991 | Desmarais |
| 5,048,544 | A | 9/1991 | Mascarelli et al. |
| 5,078,156 | A | 1/1992 | Furuya et al. |
| 5,081,158 | A | 1/1992 | Pomerantz |
| 5,089,307 | A | 2/1992 | Ninomiya et al. |
| 5,092,352 | A | 3/1992 | Sprinkle, III et al. |
| 5,097,851 | A | 3/1992 | Ehling et al. |
| 5,099,864 | A | 3/1992 | Young et al. |
| 5,101,839 | A | 4/1992 | Jakob et al. |
| 5,130,132 | A | 7/1992 | Badmajew |
| 5,135,753 | A | 8/1992 | Baker et al. |
| 5,144,966 | A | 9/1992 | Washington |
| 5,144,967 | A | 9/1992 | Cartwright et al. |
| 5,147,654 | A | 9/1992 | Place et al. |
| 5,166,233 | A | 11/1992 | Kuroya et al. |
| 5,186,185 | A | 2/1993 | Mashiko et al. |
| 5,197,494 | A | 3/1993 | Kramer |
| D335,934 | S | 5/1993 | Howard |
| 5,240,016 | A * | 8/1993 | Nichols et al. ............ 131/335 |
| 5,244,668 | A | 9/1993 | Snipes |
| 5,284,163 | A | 2/1994 | Knudsen et al. |
| 5,288,498 | A | 2/1994 | Stanley et al. |
| 5,307,821 | A | 5/1994 | Misuda et al. |
| 5,327,917 | A | 7/1994 | Lekwauwa et al. |
| 5,353,816 | A | 10/1994 | Ehling et al. |
| 5,358,765 | A | 10/1994 | Markulin |
| 5,360,024 | A | 11/1994 | Greig |
| 5,387,416 | A | 2/1995 | White et al. |
| 5,393,528 | A | 2/1995 | Staab |
| 5,405,366 | A | 4/1995 | Fox et al. |
| 5,411,945 | A | 5/1995 | Ozaki et al. |
| 5,433,960 | A | 7/1995 | Meyers |
| 5,441,060 | A | 8/1995 | Rose et al. |
| 5,455,053 | A | 10/1995 | Zimmermann et al. |
| 5,456,745 | A | 10/1995 | Roreger et al. |
| 5,470,581 | A | 11/1995 | Grillo et al. |
| 5,480,973 | A | 1/1996 | Goodlad et al. |
| 5,484,604 | A | 1/1996 | Solomon et al. |
| 5,487,902 | A | 1/1996 | Andersen et al. |
| 5,488,962 | A | 2/1996 | Perfetti |
| 5,500,647 | A | 3/1996 | Carrara |
| 5,518,730 | A | 5/1996 | Fuisz |
| 5,518,902 | A | 5/1996 | Ozaki et al. |
| 5,525,351 | A | 6/1996 | Dam |
| 5,529,782 | A | 6/1996 | Staab |
| 5,533,530 | A | 7/1996 | Young et al. |
| 5,543,164 | A | 8/1996 | Krochta et al. |
| 5,547,693 | A | 8/1996 | Krochta et al. |
| 5,549,906 | A | 8/1996 | Santus |
| 5,556,635 | A | 9/1996 | Istin et al. |
| 5,558,199 | A | 9/1996 | Roether et al. |
| 5,562,108 | A | 10/1996 | Hardy et al. |
| 5,584,306 | A | 12/1996 | Beauman et al. |
| 5,593,684 | A | 1/1997 | Baker et al. |
| 5,594,030 | A | 1/1997 | Conte et al. |
| 5,595,592 | A | 1/1997 | Signorino et al. |
| 5,599,554 | A | 2/1997 | Majeti |
| 5,599,583 | A | 2/1997 | Lew et al. |
| 5,620,757 | A | 4/1997 | Ninomiya et al. |
| 5,629,003 | A | 5/1997 | Horstmann et al. |
| 5,645,088 | A | 7/1997 | Olovson |
| 5,662,920 | A | 9/1997 | Santus |
| 5,665,442 | A | 9/1997 | Andersen et al. |
| 5,666,979 | A | 9/1997 | Chase |
| 5,687,746 | A | 11/1997 | Rose et al. |
| 5,709,913 | A | 1/1998 | Andersen et al. |
| 5,715,844 | A | 2/1998 | Young et al. |
| 5,723,163 | A | 3/1998 | Zimmermann et al. |
| 5,733,574 | A | 3/1998 | Dam |
| 5,747,648 | A | 5/1998 | Bassi et al. |
| 5,783,207 | A | 7/1998 | Stanley et al. |
| 5,785,989 | A | 7/1998 | Stanley et al. |
| 5,800,647 | A | 9/1998 | Andersen et al. |
| 5,800,832 | A | 9/1998 | Tapolsky et al. |
| 5,810,018 | A | 9/1998 | Monte |
| 5,810,961 | A | 9/1998 | Andersen et al. |
| 5,811,126 | A | 9/1998 | Krishnamurthy |
| 5,817,381 | A | 10/1998 | Chen et al. |
| 5,824,334 | A | 10/1998 | Stanley et al. |
| 5,845,648 | A | 12/1998 | Martin |
| 5,853,760 | A | 12/1998 | Cremer |
| 5,908,034 | A | 6/1999 | Adedeji |
| 5,914,118 | A | 6/1999 | Yamamura et al. |
| 5,924,430 | A | 7/1999 | Baldauf |
| 5,939,100 | A | 8/1999 | Albrechtsen et al. |
| 5,947,128 | A | 9/1999 | Adedeji |
| 5,948,430 | A | 9/1999 | Zerbe et al. |
| 5,958,480 | A | 9/1999 | Eggink et al. |
| 5,962,053 | A | 10/1999 | Merritt, II |
| 5,965,708 | A | 10/1999 | Bassi et al. |
| 5,977,312 | A | 11/1999 | Bassi et al. |
| 6,001,346 | A | 12/1999 | Delwiche et al. |
| 6,030,673 | A | 2/2000 | Andersen et al. |
| 6,041,789 | A | 3/2000 | Bankert et al. |
| 6,079,418 | A | 6/2000 | Russo |
| 6,082,368 | A | 7/2000 | Brown |
| 6,082,370 | A | 7/2000 | Russo |
| 6,083,531 | A | 7/2000 | Humbert-Droz et al. |
| 6,083,582 | A | 7/2000 | Chen et al. |
| 6,083,586 | A | 7/2000 | Andersen et al. |
| 6,095,152 | A | 8/2000 | Beven et al. |
| 6,110,495 | A | 8/2000 | Dam |
| 6,117,096 | A | 9/2000 | Hassard |
| 6,117,437 | A | 9/2000 | Roreger |
| 6,135,120 | A | 10/2000 | Löfman et al. |
| 6,159,498 | A | 12/2000 | Tapolsky et al. |
| 6,177,096 | B1 | 1/2001 | Zerbe et al. |
| 6,183,775 | B1 | 2/2001 | Ventouras |
| 6,210,699 | B1 | 4/2001 | Acharya et al. |
| 6,224,897 | B1 | 5/2001 | Reitberg |
| 6,231,957 | B1 | 5/2001 | Zerbe et al. |
| 6,248,760 | B1 | 6/2001 | Wilhelmsen |
| 6,264,981 | B1 | 7/2001 | Zhang et al. |
| 6,280,761 | B1 | 8/2001 | Santus |
| 6,280,769 | B1 | 8/2001 | D'Amelia et al. |
| 6,284,264 | B1 | 9/2001 | Zerbe et al. |
| 6,326,022 | B1 | 12/2001 | Katz |
| 6,333,048 | B1 | 12/2001 | Asmussen et al. |
| 6,344,222 | B1 | 2/2002 | Cherukuri et al. |
| 6,379,726 | B1 | 4/2002 | Tomasula |
| 6,403,130 | B2 | 6/2002 | Beyer |
| 6,419,903 | B1 | 7/2002 | Xu et al. |
| 6,432,448 | B1 | 8/2002 | Augello et al. |
| 6,479,076 | B2 | 11/2002 | Blank |
| 6,497,899 | B2 | 12/2002 | Thombre et al. |
| 6,500,462 | B1 | 12/2002 | Augello et al. |
| 6,552,024 | B1 | 4/2003 | Chen et al. |
| 6,576,298 | B2 | 6/2003 | Bennett et al. |
| 6,583,160 | B2 | 6/2003 | Smith et al. |
| 6,592,887 | B2 | 7/2003 | Zerbe et al. |
| 6,595,209 | B1 | 7/2003 | Rose et al. |
| 6,596,298 | B2 | 7/2003 | Leung et al. |
| 6,649,188 | B2 | 11/2003 | Gilleland et al. |

(56) References Cited

U.S. PATENT DOCUMENTS

| | | |
|---|---|---|
| 6,656,493 B2 | 12/2003 | Dzija et al. |
| 6,660,302 B1 | 12/2003 | Geyser, Jr. et al. |
| 6,668,839 B2 | 12/2003 | Williams |
| 6,676,959 B1 | 1/2004 | Andersson et al. |
| 6,699,315 B2 | 3/2004 | Augello et al. |
| 6,709,671 B2 | 3/2004 | Zerbe et al. |
| 6,709,713 B2 | 3/2004 | Augello et al. |
| 6,723,342 B1 | 4/2004 | Augello et al. |
| 6,737,080 B1 | 5/2004 | Schumann |
| 6,740,332 B2 | 5/2004 | Zyck et al. |
| 6,742,525 B2 | 6/2004 | Sinclair, Jr. |
| 6,749,882 B2 | 6/2004 | Fortune, Jr. |
| 6,834,654 B2 | 12/2004 | Williams |
| 6,845,777 B2 | 1/2005 | Pera |
| 6,881,449 B2 | 4/2005 | Augello et al. |
| 6,884,288 B2 | 4/2005 | Gayser, Jr. et al. |
| 6,887,307 B1 | 5/2005 | Scott et al. |
| 6,902,609 B2 | 6/2005 | Steffenino et al. |
| 6,902,783 B1 | 6/2005 | Hammer et al. |
| 6,903,841 B2 | 6/2005 | Spurgeon et al. |
| 6,906,043 B2 | 6/2005 | Awamura et al. |
| 6,923,981 B2 | 8/2005 | Leung et al. |
| 6,932,861 B2 | 8/2005 | Augello |
| 6,936,291 B1 | 8/2005 | Weibel |
| 6,953,040 B2 | 10/2005 | Atchley et al. |
| 7,025,983 B2 | 4/2006 | Leung et al. |
| 7,032,601 B2 | 4/2006 | Atchley et al. |
| 7,097,669 B2 | 8/2006 | Stephens et al. |
| 7,097,869 B2 | 8/2006 | Hayabuchi et al. |
| 7,105,173 B1 | 9/2006 | Rolling |
| 7,332,230 B1 | 2/2008 | Krumme |
| 904,521 A1 | 11/2008 | Ellis |
| 2002/0022057 A1 | 2/2002 | Battey et al. |
| 2002/0059939 A1 | 5/2002 | Fox |
| 2002/0119192 A1 | 8/2002 | Vishwanathan et al. |
| 2002/0131990 A1 | 9/2002 | Barkalow et al. |
| 2002/0147201 A1 | 10/2002 | Chen et al. |
| 2002/0162562 A1 | 11/2002 | Williams |
| 2002/0162563 A1 | 11/2002 | Williams |
| 2002/0170567 A1 | 11/2002 | Rizzotto et al. |
| 2003/0008008 A1 | 1/2003 | Leung et al. |
| 2003/0029444 A1 | 2/2003 | Carbone et al. |
| 2003/0053962 A1 | 3/2003 | Zerbe et al. |
| 2003/0068331 A1 | 4/2003 | Battaglia et al. |
| 2003/0068376 A1 | 4/2003 | Chen et al. |
| 2003/0084912 A1 | 5/2003 | Pera |
| 2003/0098033 A1 | 5/2003 | Macadam et al. |
| 2003/0099692 A1 | 5/2003 | Lydzinski et al. |
| 2003/0107149 A1 | 6/2003 | Yang et al. |
| 2003/0111088 A1 | 6/2003 | Fox |
| 2003/0129238 A1 | 7/2003 | Augello et al. |
| 2003/0161913 A1 | 8/2003 | Stewart |
| 2003/0176467 A1 | 9/2003 | Andersson et al. |
| 2003/0206942 A1 | 11/2003 | Kulkarni et al. |
| 2003/0211136 A1 | 11/2003 | Kulkarni et al. |
| 2003/0224090 A1 | 12/2003 | Pearce et al. |
| 2003/0235630 A1 | 12/2003 | Nussen |
| 2004/0020503 A1 | 2/2004 | Williams |
| 2004/0043134 A1 | 3/2004 | Corriveau et al. |
| 2004/0052839 A1 | 3/2004 | Archibald et al. |
| 2004/0052853 A1 | 3/2004 | Clark |
| 2004/0081713 A1 | 4/2004 | Maxwell et al. |
| 2004/0086539 A1 | 5/2004 | Pinna et al. |
| 2004/0086546 A1 | 5/2004 | Maxwell et al. |
| 2004/0087467 A1 | 5/2004 | MacQuarrie |
| 2004/0096569 A1 | 5/2004 | Barkalow et al. |
| 2004/0107971 A1 | 6/2004 | De |
| 2004/0112394 A1 | 6/2004 | Krukonis et al. |
| 2004/0115137 A1 | 6/2004 | Verrall et al. |
| 2004/0118421 A1 | 6/2004 | Hodin et al. |
| 2004/0118422 A1 | 6/2004 | Lundin et al. |
| 2004/0120991 A1 | 6/2004 | Gardner et al. |
| 2004/0126330 A1 | 7/2004 | Awamura et al. |
| 2004/0131662 A1 | 7/2004 | Davidson et al. |
| 2004/0136923 A1 | 7/2004 | Davidson |
| 2004/0137040 A1 | 7/2004 | Nogami |
| 2004/0137043 A1 | 7/2004 | Augello et al. |
| 2004/0141927 A1 | 7/2004 | Johnson et al. |
| 2004/0146599 A1 | 7/2004 | Andersen et al. |
| 2004/0156794 A1 | 8/2004 | Barkalow et al. |
| 2004/0166214 A1 | 8/2004 | Gesford et al. |
| 2004/0180110 A1 | 9/2004 | Mistry |
| 2004/0191322 A1 | 9/2004 | Hansson |
| 2004/0202698 A1 | 10/2004 | Ramji et al. |
| 2004/0208931 A1 | 10/2004 | Friend et al. |
| 2004/0213848 A1 | 10/2004 | Li et al. |
| 2004/0241294 A1 | 12/2004 | Barabolak et al. |
| 2004/0247646 A1 | 12/2004 | Ivory et al. |
| 2004/0247647 A1 | 12/2004 | Ivory et al. |
| 2004/0247648 A1 | 12/2004 | Fadden et al. |
| 2004/0247649 A1 | 12/2004 | Pearce et al. |
| 2004/0247744 A1 | 12/2004 | Pearce et al. |
| 2004/0253189 A1 | 12/2004 | Maxwell et al. |
| 2004/0253190 A1 | 12/2004 | Maxwell et al. |
| 2004/0253191 A1 | 12/2004 | Maxwell et al. |
| 2004/0253192 A1 | 12/2004 | Maxwell et al. |
| 2004/0253278 A1 | 12/2004 | Maxwell et al. |
| 2004/0258630 A1 | 12/2004 | Boyd et al. |
| 2004/0258733 A1 | 12/2004 | Maxwell et al. |
| 2005/0008735 A1 | 1/2005 | Pearce |
| 2005/0031675 A1 | 2/2005 | Spence Leung et al. |
| 2005/0031775 A1 | 2/2005 | Signorino et al. |
| 2005/0037055 A1 | 2/2005 | Yang et al. |
| 2005/0039767 A1 | 2/2005 | Mua et al. |
| 2005/0056294 A1 | 3/2005 | Wanna et al. |
| 2005/0058609 A1 | 3/2005 | Nazeri |
| 2005/0079253 A1 | 4/2005 | Nakamura |
| 2005/0088632 A1 | 4/2005 | Sadi et al. |
| 2005/0089548 A1 | 4/2005 | Virgalitto et al. |
| 2005/0123502 A1 | 6/2005 | Chan et al. |
| 2005/0129814 A1 | 6/2005 | Weibel |
| 2005/0186256 A1 | 8/2005 | Dihel et al. |
| 2005/0186257 A1 | 8/2005 | Manegold et al. |
| 2005/0191336 A1 | 9/2005 | Kupper et al. |
| 2005/0207993 A1 | 9/2005 | Bazemore et al. |
| 2005/0208110 A1 | 9/2005 | Singh et al. |
| 2005/0244521 A1 | 11/2005 | Strickland et al. |
| 2006/0002987 A1 | 1/2006 | Bevacqua et al. |
| 2006/0013779 A1 | 1/2006 | Dodds et al. |
| 2006/0018842 A1 | 1/2006 | Blumenthal |
| 2006/0024425 A1 | 2/2006 | Barkalow et al. |
| 2006/0037623 A1 | 2/2006 | Lawrence, Jr. |
| 2006/0039953 A1 | 2/2006 | Leung et al. |
| 2006/0045851 A1 | 3/2006 | Fitzgerald et al. |
| 2006/0191548 A1 | 8/2006 | Strickland et al. |
| 2007/0012328 A1 | 1/2007 | Winterson et al. |
| 2009/0133703 A1 | 5/2009 | Strickland et al. |
| 2009/0133704 A1 | 5/2009 | Strickland et al. |
| 2012/0199149 A1 | 8/2012 | Strickland et al. |

FOREIGN PATENT DOCUMENTS

| | | |
|---|---|---|
| CN | 1407886 A | 4/2003 |
| EP | 0 115 955 | 8/1984 |
| EP | 0 118 637 | 9/1984 |
| EP | 0 119 012 | 9/1984 |
| EP | 0 140 486 | 5/1985 |
| EP | 0 241 698 | 10/1987 |
| EP | 0 245 732 | 11/1987 |
| EP | 0 271 036 | 6/1988 |
| EP | 0 277 519 | 8/1988 |
| EP | 0 295 122 | 12/1988 |
| EP | 0 321 943 | 6/1989 |
| EP | 0 371 285 | 6/1990 |
| EP | 0 391 158 | 10/1990 |
| EP | 0 399 252 | 11/1990 |
| EP | 0 405 190 | 1/1991 |
| EP | 0450253 B1 | 10/1991 |
| EP | 0 467 658 | 1/1992 |
| EP | 0 476 349 | 3/1992 |
| EP | 0 494 784 | 7/1992 |
| EP | 0 514 151 | 11/1992 |
| EP | 0 525 347 | 2/1993 |
| EP | 0450253 | 1/1994 |

(56) References Cited

FOREIGN PATENT DOCUMENTS

| | | |
|---|---|---|
| EP | 0 956 783 | 11/1999 |
| EP | 1 304 048 | 4/2003 |
| EP | 0 906 089 | 8/2003 |
| EP | 0906089 | 8/2003 |
| GB | 1 435 304 | 5/1976 |
| JP | S50-148598 | 11/1975 |
| JP | S61-111677 | 5/1986 |
| JP | S61-163005 | 10/1986 |
| JP | S61-163005 | 1/1988 |
| JP | H05-024353 | 8/1994 |
| JP | 07-044622 | 11/1995 |
| JP | H09-505553 | 6/1997 |
| JP | H10-043211 | 2/1998 |
| JP | S63-068798 U | 5/1998 |
| JP | 2000-504028 | 4/2000 |
| JP | A2000-504028 | 4/2000 |
| JP | 2001-504106 | 3/2001 |
| JP | 3210945 | 9/2001 |
| JP | 2002-535269 | 10/2002 |
| JP | 2003-513906 | 4/2003 |
| JP | 2004501966 | 1/2004 |
| JP | 2005-112845 | 4/2005 |
| WO | WO 91/09599 | 7/1991 |
| WO | WO 91/16041 | 10/1991 |
| WO | WO 95/01788 | 1/1995 |
| WO | WO 95/03050 | 2/1995 |
| WO | WO 96/00070 | 1/1996 |
| WO | WO 96/07336 | 3/1996 |
| WO | WO 96/10342 | 4/1996 |
| WO | WO 97/12605 | 4/1997 |
| WO | WO 97/42941 | 11/1997 |
| WO | WO 98/20862 | 5/1998 |
| WO | WO 99/04764 | 2/1999 |
| WO | WO 99/15171 | 4/1999 |
| WO | WO 99/24020 | 5/1999 |
| WO | WO 99/39595 | 8/1999 |
| WO | WO 99/55371 | 11/1999 |
| WO | WO 00/30641 | 6/2000 |
| WO | WO 00/32043 | 6/2000 |
| WO | WO 00/42992 | 7/2000 |
| WO | WO 00/67694 | 11/2000 |
| WO | WO 01/34121 | 5/2001 |
| WO | WO 01/37814 | 5/2001 |
| WO | WO 01/70194 | 9/2001 |
| WO | WO 01/89476 | 11/2001 |
| WO | WO0202096 | 1/2002 |
| WO | WO 02/38208 | 5/2002 |
| WO | WO 02/063982 | 8/2002 |
| WO | WO 02/076211 | 10/2002 |
| WO | WO 02/087365 | 11/2002 |
| WO | WO 03/026655 | 4/2003 |
| WO | WO 03/026656 | 4/2003 |
| WO | WO 03/028491 | 4/2003 |
| WO | WO 03/028492 | 4/2003 |
| WO | WO 03/039518 | 5/2003 |
| WO | WO 03/055337 | 7/2003 |
| WO | WO 03/097000 | 11/2003 |
| WO | WO 2004/009050 | 1/2004 |
| WO | WO 2004/009445 | 1/2004 |
| WO | WO 2004/019800 | 3/2004 |
| WO | WO 2004/019885 | 3/2004 |
| WO | WO 2004/024111 | 3/2004 |
| WO | WO 2004/041283 | 5/2004 |
| WO | WO 2004/043165 | 5/2004 |
| WO | WO 2004/056218 | 7/2004 |
| WO | WO 2004/058231 | 7/2004 |
| WO | WO 2005/009386 | 2/2005 |
| WO | WO 2005/023227 | 3/2005 |
| WO | WO 2005/035385 | 4/2005 |
| WO | WO 2005/041699 | 5/2005 |
| WO | WO 2005/048965 | 6/2005 |
| WO | WO 2005/048980 | 6/2005 |
| WO | WO 2005/104881 | 11/2005 |
| WO | WO 2006/004480 | 1/2006 |
| WO | WO 2006/065192 | 6/2006 |
| WO | WO 2006/120570 | 11/2006 |
| WO | WO 2006/127772 | 11/2006 |
| WO | WO 2007/037962 | 4/2007 |
| WO | WO 2007/041035 | 4/2007 |
| WO | WO 2007/138484 | 12/2007 |
| WO | WO 2007/144687 | 12/2007 |
| WO | WO 2008/016520 | 2/2008 |
| WO | WO 2008/056135 | 5/2008 |

OTHER PUBLICATIONS

"Development of Biodegradable Water-Soluble Films From Pectin and Starch Blends," [http://les.epa.gov/ncerqa_...ther/pp/seybold.html] Last Updated Nov. 17, 1997. Grant awarded to Ken Seybold and Bioplastics, Inc from U.S. Dept. of Agriculture.
"Edible Films Solve Problems," *Food Technology*, 1997, 51(2):60.
"Edible Pouches Aid Easy Mixing for Bakery Plants," reprinted from *Package Engineering*, Sep. 1977.
"Edible Soy Protein Film Could Replace Plastic Wrap," *Delta Farm Press*, Feb. 15, 2002.
"Edisol-M," Product Information, Polymer Films Inc.
"Fabricated Food Products Based on Thermoplastic Klucel" Hercules Incorporated.
"Hydroxypropyl Cellulose: Properties and Uses," Product Information, Hercules Klucel.
Industry News: Osaka Kagaku Gokin Expands Edible Plastic Activities; *New Food Products in Japan*, Sep. 15, 1998.
"Klucel Water-Soluble Thermoplastic," Product Information, Hercules Incorporated.
"New Face in the Film Field," reprinted from *Chemical Week*, Oct. 21, 1961.
"New Packaging Technologies Developing at Clemson," *ClemsoNews*, 1997 [http://clemsonews.clemson.edulWWW_releases/1997/November1997/Packaging_Research.html] Downloaded Feb. 16, 2000.
"Preliminary Product Information MONO-SOLO MC-1257 Water Soluble Film," Chris Craft Industrial Products, Inc.
"Protecting Delicate Decorations," *Packaging World*, p. 8.
"Rice and Pullulan Form Edible Films," *Food Ingredient News*, vol. 3, Mar. 22, 1997.
"Tobacco in History," (1998) [http:l/www.ephidrina.org/tobacco/history.html] Downloaded Feb. 6, 2006.
"United States Tobacco Co. Makes First Change in 422 Years of Snuff," Western Tobacco Journal, Apr. 14, 1960.
"Using Water Soluble Plastics," *Manufacturing Chemist & Aerosol News*, 1980, 49:53.
"Water Soluble Films," Polymer Films Inc.
"Zein Films," [http://www.arserrc.gov/es/zeinflms.htm] Downloaded Dec. 28, 1999.
Acevedo, "The Future of Water-Soluble Film," *Flexible Packaging*, Jul. 2001, pp. 30-31.
American Tobacco, The Vaporette Inhaler System, Loaded to tobaccodocuments.org on Nov. 23, 1998.
Batdorf et al., "Hydroxyethyl Cellulose as a Building Raw Material," Nair, Chemical Additives, Ed., A Symposium Sponsored by the Division of Chemical Marketing and Economics at the 161st Meeting of the American Chemical Society, Los Angeles, California, Mar. 29-31, 1971 New York, American Chemical Society, Division of Chemical Marketing and Economics, pp. 136-141.
Bone-healthy Breath Strips Win Project SOY, 2003, Campus News University of Guelph http://www.uoguelph.ca/mediarel/archives/002547.html) Downloaded Jun. 2, 2003.
Borio, "The Tobacco Timeline," [http://www.tobacco.org/HistoryfTobacco_History.html] Downloaded Feb. 6, 2006.
Brown & Williamson Tobacco Corporation Internal Correspondence, Dated Dec. 20, 1984.
Brown & Williamson Tobacco Corporation Research & Development Internal Correspondence, Dated Oct. 6, 1992.
Brown & Williamson Tobacco Corporation Research & Development Internal Correspondence, Dated May 15, 1995.
Brown & Williamson Tobacco Corporation Research, Development & Engineering Meeting Report, Dated Apr. 24, 1986.
Cagri et al., Mechanical, Barrier and Antimicrobial Properties of Low pH Whey Protein Isolate Edible Films Containing p-Aminobenzoic Acid or Sorbic Acid; The IFT Annual Meeting 1999 [http://www.

(56) References Cited

OTHER PUBLICATIONS confex2.comlift199annual/abstracts/3944.htm] Downloaded Feb. 16, 2000.
Desmarais et al., "Hydroxyalkyl and Ethyl Ethers of Cellulose," *Industrial Gums: Polysaccharides and Their Derivatives*, 1993, Chapter 19, Whistler and BeMiller, Ed., Academic Press, pp. 505-535.
Desmarais et al., "Relationship of Chemical Structure of Water-Soluble Cellulose Ethers to Physical Properties," *The Chemistry and Rheology of Water Soluble Gums and Colloids; Comprising Papers (with Discussions)*, 1966, SCI Monograph, 24:57-67.
Desmarais, "Hydroxyalkyl Derivatives of Cellulose," Whistler and BeMiller, Ed., Chapter XXIX of *Industrial Gums: Polysaccharides and Their Derivatives*, 1973, Academic Press, pp. 649-672.
Fishman, "Edible and Biodegradable Polymer Films: Challenges and Opportunities," *Food Technology*, 1997, 51(2):16.
Givan et al., "Flue-Cured Tobacco Contracting (Direct Marketing)", The University of Georga College of Agricultural & Environmental Sciences Cooperative Extension Service, http://www.ces.uga.edu/Agriculture/agecon/pubs/comm/tobaccocontract.htm, accessed Mar. 6, 2009 at 12:46 PM Eastern Time.
Hanners, ASH on New Secret Memo Helping FDA, http://www.no-smoking.org/may99/05-24-99-2.html, Dated May 23, 1999.
Hasenfratz et al. "Nicotine Absorption and the Subjective and Physiologic Effects of Nicotine Toothpicks," *Clin Pharmacol Ther.*, 1991, 50:456-461.
Hershko et al., "Relationships Between Edible Coatings and Garlic Skin," *J. Food Sci.*, 1996, 61:769-777.
Klahorst, "Credible Edible Films," Food Product Design, 1999 [http://www.foodproductdesign.com/archive/1999/0999ap.html] Downloaded Feb. 24, 2000.
Krochta et at., "Edible and Biodegradable Polymer Films: Challenges and Opportunities," *Food Technology*, 1997, 51(2):61-74.
LaBell, "Edible Packaging," *Food Processing*, pp. 25-26.
Letter Covering the Subject of Water-Soluble Klucel Film from J. M. Rossman to Frank A. Ross. Dated Sep. 27, 1972 and table.
McHugh et al., "Permeability Properties of Fruit Puree Edible Films," *J. Food Sci.*, 1996, 61:88-91.
McHugh et al., "Plasticized Whey Protein Edible Films: Water Vapor Permeability Properties," *J. Food Sci.*, 1994, 59:416-419, 423.
Park et al., "Application of Laminated Edible Films to Potato Chip Packaging," *J. Food Sci.*, 1996, 61:766-768, 777.
Park et al., "Fatty Acid Distribution and Its Effect on Oxygen Permeability in Laminated Edible Films," *J. Food Sci.*, 1996, 61:401-406.
Park et al., Permeability and Mechanical Properties of Cellulose-Based Edible Films, *J. Food Sci.*, 1993, 58:1361-1364, 1370.
Philip Morris Brainstorming Session, Dated Aug. 21, 1990.
Rice, "What's New in Edible Films? Industry, Academia and Government Researchers Continue to Be Fascinated by the Possibilities of Eating Away Packaging Waste," *Food Processing*, Jul. 1994, pp. 61-62.
RJ Reynolds Brainstorming Ideas—Scientist Group, Dated Jan. 27, 1993.
Rodu et al., "Clinical and Chemical Properties of a Novel Mucosal Bioadhesive Agent," *J. Oral Pathol.*, 1988, 17:564-567.
Rossman et al., "The Case for the Disappearing Comb," *Hercules Chemist*, 1970, 61:9-15.
Rossman, "Now: a Plastic to Eat- or Simply Dissolve in Water," *Package Engineering*, Jul. 1971.
Rossman, "The Latest Water-Soluble Films Point Up New Performance Levels," *Package Engineering*, Jul. 1976.
Rudgley, "Tobacco," *The Encyclopedia of Psychoactive Substances*, 1998, [http://www.biopsychiatry.com/tobacco/] Downloaded Feb. 6, 2006.
Shih, "Edible Films from Rice Protein Concentrate and Pullulan," *Cereal Chem.*, 1996, 73:406-409.
Sigma-Aldrich, "Search Results, We Found 3 Products That Match Your Search for nicotine salts", Sigma-Aldrich, Co., accessed Mar. 6, 2009.
Watson et al., "Achieving Method Simplification Through the Use of Water-Soluble-Film Pouches," reprinted from Modern Packaging, Apr. 1962.
Weeks, "Relationship Between Leaf Chemistry and Organoleptic Properties of Tobacco Smoke," *Tobacco: Production, Chemistry and Technology*, 1999, Davis and Nielsen (eds.), pp. 304-312.
International Search Report and Written Opinion of the International Searching Authority from PCT/US2004/036793, mailed Jun. 27, 2006.

* cited by examiner

TOBACCO COMPOSITIONS

CROSS-REFERENCE TO RELATED APPLICATIONS

This application is a Divisional application of and claims benefit under 35 U.S.C. §121 to U.S. application Ser. No. 10/982,248, filed Nov. 5, 2004, which claims benefit under 35 U.S.C. §119(e) of U.S. Provisional Application No. 60/518,352, filed Nov. 7, 2003, and U.S. Provisional Application No. 60/603,888, filed Aug. 23, 2004, each of which is hereby incorporated by reference.

FIELD OF THE INVENTION

The invention relates to the field of tobacco products.

SUMMARY OF THE INVENTION

The invention features tobacco compositions and methods of their use and manufacture. Compositions of the invention may be based on a variety of technologies. Technologies include films, tabs, shaped parts, gels, consumable units, insoluble matrices, and hollow shapes. In addition to tobacco, compositions may also contain flavors, colors, and other additives as described herein. Compositions may also be orally disintegrable. Exemplary compositions and methods of their manufacture are described herein.

For example, any composition described herein may include a flavor or flavor masking agent. Exemplary flavors include licorice, kudzu, hydrangea, Japanese white bark magnolia leaf, chamomile, fenugreek, clove, menthol, Japanese mint, aniseed, cinnamon, herb, wintergreen, cherry, berry, apple, peach, Dramboui, bourbon, scotch, whiskey, spearmint, peppermint, lavender, cardamon, apium graveolens, cascarilla, nutmeg, sandalwood, bergamot, geranium, honey essence, rose oil, vanilla, lemon oil, orange oil, cassia, caraway, cognac, jasmin, ilangilang, sage, fennel, piment, ginger, anise, coriander, coffee, or a mint oil from any species of the genus *Mentha*.

Any composition of the invention may also include a sweetener (such as sucrose, sucralose, acesulfame potassium, aspartame, saccharine, cyclamates, lactose, sucrose, glucose, fructose, sorbitol, and mannitol); a surfactant; a plasticizer (such as glycerine, propylene glycol, polyethylene glycol, sorbitol/mannitol, acetylated monoglycerides, triacetin, and 1,3 butane diol); a filler (such as starch, microcrystalline cellulose, wood pulp, soluble fiber, calcium carbonate, dicalcium phosphate, calcium sulfate, and a clay); a lubricant (such as stearic acid and a stearate) or a wax (such as lecithin, glycerol monostearate, and propylene glycol monostearate); a preservative (such as methyl paraben and potassium sorbate); and/or a stabilizer (such as ascorbic acid, monosterol citrate, BHT, and BHA).

Any composition described herein may further include a coating, e.g., matte or glossy. The coating preferably includes a color, flavor, sweetener, or flavor masking agent. The coating may also include a different flavor, color, or rate of disintegration from the format in the composition. The coating may also include tobacco.

Any composition described herein may further include a printed pattern, e.g., in a logo. A printed pattern may include a color, tobacco, a flavor, sweetener, or flavor masking agent. The surface of any composition described herein may also include a pattern in relief.

Tobacco included in any composition may be a powder, granules, shreds, or perceived to be soluble in the mouth.

Any composition described herein may further include flakes, e.g., containing tobacco or a plurality of flavors or colors.

Any composition of the invention may be formed in a shape suitable for application in the mouth. A composition of the invention may further provide tobacco satisfaction, e.g., over a period of 10 s to 30 minutes.

The invention also features a method for obtaining tobacco satisfaction by placing at least a portion of any composition as described herein in the mouth.

The invention also features methods for making compositions as described herein. Any of these methods may further include adding a coating to the composition, e.g., by spraying, brushing, roll coating, doctor bar casting, slot coating, extrusion coating, or hot melt deposition. Any of the methods may also include printing a pattern on the composition, e.g., by offset, flexographic, gravure, ink jet, laser, or screen printing. In addition, the methods of making compositions may include adding a flavor, color, flavor masking agent, or any other ingredient described herein to the format or composition.

By "format" is meant an ingredient or compilation of ingredients, as provided herein, in a composition, for example, a carrier or agent.

By "tobacco" is meant any part, e.g., leaves, flowers, roots, and stems, of any member of the genus *Nicotiana*. Exemplary species of tobacco include *N. rustica* and *N. tabacum* (e.g., LA B21, LN KY171, TI 1406, Basma, Galpao, Perique, Beinhart 1000-1, and Petico). Other species include *N. acaulis, N. acuminata, N acuminata* var. *multiflora, N. africana, N. alata, N. amplexicaulis, N. arentsii, N. attenuata, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*. The tobacco may be whole, shredded, cut, cured, aged, fermented, or otherwise processed, e.g., granulated or encapsulated. Tobacco may also be in the form of finished products, including but not limited to any non-combustible tobacco that is orally consumed, e.g., smokeless tobacco. Such smokeless tobacco includes snuff (moist or dry), chewing tobacco, loose tobacco, pouched tobacco, and the like, or any form contained herein. The term also includes an extract of tobacco including two or more tobacco organoleptic components.

By "tobacco satisfaction," in this case, is meant the experience associated with tobacco organoleptic components and added flavor components that are released in the mouth when using a smokeless tobacco. An adult consumer who chooses to use a smokeless tobacco product purchases a smokeless tobacco product typically according to their individual preference, such a preference includes, without limitation, flavor, cut of tobacco, form, ease of use, and packaging.

By "organoleptic" is meant relating or contributing to the integrated sensory perception by the consumer that includes, for example, any combination of aroma, fragrance, flavor, taste, odor, mouth feel, or the like.

By "non-combustible" is meant does not combust during ordinary usage.

Compositions described herein are advantageous from the perspective of size, ease of use, and controlled rate of disintegration.

All percentages are by weight unless otherwise noted.

Other features and advantages will be apparent from the following description and the claims.

DETAILED DESCRIPTION OF THE INVENTION

The invention features tobacco compositions that are typically for tobacco satisfaction.

A. Tobacco

Tobacco useful in compositions described herein includes any raw or processed form, e.g., a powder, granule, or shred. Preferably, the tobacco is sized or made to disintegrate in the mouth (e.g., dissolve), to give the perception of dissolvability (e.g., the tobacco does not produce a tactile experience in the mouth), or to be easily swallowed. Alternatively, the tobacco may be sized or made to provide a tactile experience in the mouth. Exemplary average sizes are in the range of 1 to 1000 μm, e.g., about 800, 500, 250, 100, 80, 75, 50, 25, 20, 15, 10, 8, 6, 5, 3, 2, or 1 μm or less, preferably 80 μm or less. The tobacco may also be in the form of a slurry or a flowable gel. A flowable gel is a mixture of a format dissolved in water and mixed with tobacco and then mixed with a miscible solvent that prevents the complete dissolution of the format. Such a mixture causes the format to swell forming a viscous paste that is pseudoplastic and is easily dispensed from a container (e.g., a tube) with slight pressure. An exemplary tobacco is smokeless tobacco. Additional tobaccos are described in U.S. Publication Nos. 2003/0094182 and 2003/0070687, U.S. Ser. No. 60/603,887, and U.S. Ser. No. 10/981,948 titled "*Nicotiana* Compositions," filed Nov. 5, 2004; the disclosures of which are hereby incorporated by reference. The tobacco employed in the composition may also be prepared according to the methods of U.S. Publication No. 2004/0112394; the disclosure of which is hereby incorporated by reference. Other suitable tobacco is known in the art.

Tobacco may be distributed randomly or evenly throughout a composition or concentrated in various regions thereof, e.g., in the center or on the surface.

Depending on the desired characteristics and the end use of the composition, the typical final tobacco concentration ranges from 1 percent to 99 percent by weight of the final composition, for example, at most 10, 15, 20, 25, 30, 35, 40, 45, 50, 55, 60, 65, 70, 75, 80, 85, or 90%. In preferred embodiments, the composition includes around 25% tobacco.

B. Compositions

In general, compositions of the invention are intended for oral use or consumption. A composition containing tobacco may be manufactured using any suitable orally compatible format. The tobacco may be mixed directly with the format or otherwise supported by the format. For example, a composition may contain tobacco, e.g., as dried particles, shreds, granules, a powder, or a slurry, deposited on, mixed in, surrounded by, or otherwise combined with a format. Tobacco in compositions may or may not be, or be perceived to be, soluble. In one embodiment, the compositions are spitless tobacco compositions. Compositions may also include a mixture of forms or types of tobacco. Compositions may be foamed or dense. Foamed compositions may be rigid or flexible and may be based on water soluble, water insoluble, or thermoplastic formats. Exemplary compositions are described herein. In one embodiment, a composition of the invention is non-combustible.

Formats suitable for use in the compositions described herein include orally compatible polymers, such as cellulosics (e.g., carboxymethyl cellulose (CMC), hydroxypropyl cellulose (HPC), hydroxyethyl cellulose (HEC), hydroxypropyl methyl cellulose (HPMC), and methyl cellulose (MC)), natural polymers (e.g., starches and modified starches, konjac, collagen, inulin, soy protein, whey protein, casein, and wheat gluten), seaweed-derived polymers (e.g., carrageenan (kappa, iota, and lambda), alginates, and propylene glycol alginate), microbial-derived polymers (e.g., xanthan, dextran, pullulan, curdlan, and gellan), extracts (e.g., locust bean gum, guar gum, tara gum, gum tragacanth, pectin (lo methoxy and amidated), agar, zein, karaya, gelatin, psyllium seed, chitin, and chitosan), exudates (e.g., gum acacia (arabic) and shellac), synthetic polymers (e.g., polyvinyl pyrrolidone, polyethylene oxide, and polyvinyl alcohol). Other useful formats are known in the art, for example, see Krochta et al. *Food Technology*, 1997, 51:61-74, Glicksman *Food Hydrocolloids* CRC 1982, Krochta *Edible Coatings and Films to Improve Food Quality* Technomic 1994, *Industrial Gums* Academic 1993, Nussinovitch *Water-Soluble Polymer Applications in Foods* Blackwell Science 2003. Depending on the desired characteristics, a composition may also include fillers (e.g., starch, microcrystalline cellulose, wood pulp (e.g., Solkafloc from International Fibers, Inc.), soluble fiber (e.g., Fibersol from Matsushita), calcium carbonate, dicalcium phosphate, calcium sulfate, and clays), lubricants (e.g., lecithin, stearic acid, stearates (e.g., Mg or K), and waxes (e.g., glycerol monostearate, propylene glycol monostearate, and acetylated monoglycerides)), plasticizers (e.g., glycerine, propylene glycol, polyethylene glycol, sorbitol, mannitol, triacetin, and 1,3 butane diol), stabilizers (e.g., ascorbic acid and monosterol citrate, BHT, or BHA), or other compounds (e.g., vegetable oils, surfactants, and preservatives). Some compounds function as both plasticizers and lubricants.

Compositions of the invention may include flavor extracts (e.g., licorice, kudzu, hydrangea, Japanese white bark magnolia leaf, chamomile, fenugreek, clove, menthol, Japanese mint, aniseed, cinnamon, herb, wintergreen, cherry, berry, peach, apple, Dramboui, bourbon, scotch, whiskey, spearmint, peppermint, lavender, cardamon, apium graveolens, cascarilla, nutmeg, sandalwood, bergamot, geranium, honey essence, rose oil, vanilla, lemon oil, orange oil, cassia, caraway, cognac, jasmin, ilangilang, sage, fennel, piment, ginger, anise, coriander, coffee, or a mint oil from any species of the genus *Mentha*), flavor masking agents, bitterness receptor site blockers, receptor site enhancers, sweeteners (e.g., sucralose, acesulfame potassium (Ace-K), aspartame, saccharine, cyclamates, lactose, sucrose, glucose, fructose, sorbitol, and mannitol), and other desirable additives such as chlorophyll, minerals, botanicals, or breath freshening agents.

Flavors may also be provided by plant matter, e.g., mint leaves, which are typically 10% flavor oils and 90% insoluble fiber. Exemplary plants further include licorice, kudzu, hydrangea, Japanese white bark magnolia, chamomile, fenugreek, clove, Japanese mint, cinnamon, herb, cherry, berry, peach, apple, lavender, cardamon, apium graveolens, cascarilla, nutmeg, sandalwood, bergamot, geranium, rose, vanilla, lemon, orange, cassia, caraway, jasmin, ilangilang, sage, fennel, piment, ginger, anise, coriander, coffee, or any species of the genus *Mentha*.

Flavor may be provided to a composition as described herein by flavor extracts, plant matter, or a combination thereof. In addition to natural flavor extracts, flavor may also be provided by imitation, synthetic, or artificial flavor ingredients and blends containing such ingredients. Flavors may be added as a powder, an oil, or in encapsulated form.

In certain embodiments, the composition disintegrates in the mouth. Disintegration rates of compositions may vary from 60 minutes to less than 1 minute. Fast release compositions typically disintegrate in under 2 minutes and most preferably, in 1 minute or less, e.g., less than 60 s, 50 s, 45 s, 40 s, 35 s, 30 s, 25 s, 20 s, 15 s, 10 s, 5 s, 4 s, 3 s, 2 s, or 1 s. The disintegration may occur by any mechanism, for example, dissolution, melting, mechanical disruption (e.g., from chewing), enzymatic or other chemical degradation, or disruption of the interaction between the format and tobacco. The format or tobacco itself may similarly disintegrate. The amount of time required for a composition to disintegrate may be controlled by varying the thickness of the composition and is dependent upon the type of format, other additives, and the pattern of usage. When placed in the mouth, the composition may temporarily adhere to a part of the oral mucosa. In addition, the length of time of the tobacco satisfaction may vary. This length of time may be affected by, e.g., by the rate of disintegration of a composition, the rate of extraction of organoleptic components from a composition, and the residence time of the composition in the mouth. The tobacco satisfaction may be provided over a period of at least 10 s, 30 s, 45 s, 1 min 2 min 3 min 5 min 10, min 15 min, 30 min, or 1 h, preferably from 10 s to 10 minutes and more preferably from 30 s to 5 minutes.

In other embodiments, the compositions do not disintegrate over the residence period in the mouth. In such compositions, introduction of tobacco organoleptic components into the mouth may occur by dissolution, leaching, extraction, or mechanical disruption caused by chewing.

Individual compositions may be sized to fit entirely in the mouth, or they may be sized to fit only partially in the mouth. Preferred cross sections of the compositions include, but are not limited to, square, circular, rectangular, elliptical, oval, and the like. Preferred dimensions may vary depending upon the serving size and ingredients. Typically, the largest dimension of a single serving is 5 cm or smaller. Alternatively, tobacco products may be made in a larger form, from which individual servings may be cut or otherwise separated, e.g., by chewing, biting, or oral disintegration. For example, a strip, or other long piece, may be placed in a container, and the consumer may remove a desired serving size. A larger composition (or orally sized piece attached to a handle) may also be partially inserted in the mouth, similar to a toothpick or cigarette, and the consumer may suck or chew on it. In one embodiment, the larger piece is orally disintegrable and may be completely consumed over a period of time.

C. Technologies

Films.

Compositions of the invention may be formed as films that may be orally disintegrable. Such films may contain a single layer or multiple layers. A single layer film will contain tobacco, a format, and other ingredients, e.g., in a homogeneous mixture. Multilayer films may include several tobacco containing layers, e.g., with the same or different kind or size of tobacco, e.g., tobacco perceived to be soluble. Multiple layers may be laminated together. In addition, multilayer films may contain tobacco in one or more layers and other layers that contain additional ingredients, as described herein. For example, individual layers may be added for flavor, sweetness, color, rate of disintegration, or stability (e.g., during handling or during consumption). Tobacco may also be placed between two or more layers in a sandwich arrangement. One or more of the layers in the sandwich may also include tobacco. In films having multiple layers, the layers may disintegrate at the same or different rates, or a layer may not disintegrate orally. When rates of disintegration differ, the composition may provide tobacco at differing times based on the layers disintegrating. Single layer films or individual layers in multilayer films may also be foamed or aerated to provide desirable physical properties or desirable dissolution or disintegration rates.

Films may be sized to fit in the mouth as individual servings. Alternatively, larger films may be fabricated from which individual servings may be separated. For example, a film may be wrapped, or otherwise shaped, to form a hollow tube or straw, which in turn may be filled with additional material. In addition, a film, e.g., containing a high percentage of tobacco in the range of 1% to 99% based on dry weight, may be fabricated and then used in preparation of flakes or a powder for addition to other compositions, as described herein. The preferred thickness of a film is typically less than 1 mm, e.g., less than 500, 200, 100, 50, 40, 30, 20, 10, 5, 4, 3, 2, or 1 μm; preferably 5 to 125 μm.

Various methods known in the art can be used to manufacture films. The technique employed may depend on the format employed in the film. Exemplary methods include solution casting or extrusion, melt extrusion, drum drying, and calendaring. Once formed, a film may be modified, e.g., by printing or otherwise coating or decorating the surface of the film. Flavors, colors, or tobacco may be added to the surface of a film by a printing, coating, or decorative process. All printing processes known in the art, e.g., offset, flexographic, gravure, ink jet, laser, screen printing, and other typical methods, may be used. Coatings or decorative patterns may be applied to the surface of the film using processes known in the art, e.g., spraying, brushing, roll coating, doctor bar casting, slot coating, extrusion coating, hot melt deposition, depositing particles or flakes, and other typical methods. The film to be printed, coated, or decorated may or may not contain tobacco. One function of the printing, coating, or decorative pattern is to provide additional amounts of color, flavor, or tobacco to the film. Another function is to improve the dimensional stability and appearance of the film. Once the printed, coated, or decorated film has been prepared, an additional layer of film may be applied to cover, protect and seal the printed, coated, or decorated surface.

FILM EXAMPLES

The following table shows exemplary ingredients for fabricating films of the invention.

TABLE A1

|  | Exemplary (%) | Preferred (%) | Example A (%) |
| --- | --- | --- | --- |
| Water soluble polymer | 10-70 | 20-45 | 30 |
| Tobacco | 1-90 | 20-40 | 25 |
| Flavor | 1-40 | 5-15 | 10 |
| Sweetener | 0.2-6 | 2-5 | 3 |
| Fiber (Soluble or insoluble) | 2-40 | 5-20 | 9 |
| Plasticizer | 1-40 | 5-15 | 10 |
| Surfactants | 0.05-5 | 0.1-1 | 0.5 |
| Starch/Maltodextrin | 1-40 | 10-20 | 10.5 |
| Lubricant | 0.5-10 | 1-3 | 2 |

Example B

Tobacco Film

A mixture of 50 grams of K-3 (60%), K-100 (35%) and K4M (5%) grades of hydroxypropylmethyl cellulose (HPMC) from Dow Chemical are added to a beaker containing 450 grams of well agitated, deionized water which has been heated to 180° F. While mixing, 40 grams of finely ground tobacco is added to the HPMC solution along with 15 grams of microcrystalline cellulose (FMC), 17 grams of starch (B-700 from Grain Processing Corp.), 16 grams of glycerine, 0.8 grams of polysorbate 80 (Unichema), and 4 grams of propylene glycol monostearate (PGMS from Danisco). Ten grams of cinnamon flavor and 2 grams of sucralose (artificial sweetener) are added to the solution when the temperature has dropped below 100° F. Two grams of sodium carbonate is added to adjust pH to approximately 7.5. Once all ingredients have been added and have been uniformly dispersed, the mixture is place in a water bath and, with continued mixing for 30 minutes, is reduced in temperature to 65° F. Additional water is added as required to obtain a Brookfield viscosity of 5,000 centipoise at a temperature of 65° F.

A portion of this tobacco containing solution described above is then spread on a glass plate using a draw down blade with a fixed gap of 15 mils (0.015 inches). The glass plate is placed in an air circulating laboratory oven preset at a temperature of 170° F. After 30 minutes, the glass plate is removed from the oven, cooled to room temperature, and the dry film with a thickness of 2.5 mils (0.0025 inches) is removed from the glass plate. The film may then be cut into smaller pieces suitable for placing in the mouth. A 1.0 inch by 1.25 inch section of the film will typically disintegrate in the mouth in less than one minute, thereby releasing the flavor, sweetener, and tobacco. The tobacco content of this film on a dry weight basis is 25%.

Example C

Opaque, Flavored Film

Using the same procedure as Example B, a solution is prepared without the addition of tobacco. While the solution is still hot, 32 grams of a titanium dioxide dispersion (50% titanium dioxide in water) supplied by Sensient Colors and 0.01 grams of FD&C Red No. 40 lake (Sensient Colors) are added with agitation. The solution is cooled to 65° F. and is spread on a glass plate, dried, and removed from the glass plate as described in Example B. An opaque, light red film of good strength and a dry film thickness of 1.5 mils (0.015 inches) is produced.

Example D

Two Layer Film

A portion of the solution from Example B is spread on a glass plate using a draw down blade with a fixed gap of 15 mils (0.015 inches). The glass plate is placed in a laboratory oven and the film is dried as in Example B. The glass plate is removed from the oven and cooled to room temperature, but the film is not removed from the glass plate.

A portion of the solution from Example C is spread over the dry film of Example B using a draw down blade with a fixed gap of 5 mils (0.005 inches). The glass plate is placed in the laboratory oven at 170° F. for 10 minutes. The dry film with a thickness of 3 mils (0.003 inches) is removed from the glass plate. The film is distinctly two sided with a layer of brown, tobacco containing film on one side and a red, flavored film on the opposite side. A 1.0 inch by 1.25 inch section of the film will typically disintegrate in the mouth in less than one minute.

Example E

Three Layer Film

A portion of the solution from Example C is spread on a glass plate using a draw down blade with a fixed gap of 5 mils and is dried in the laboratory oven as before. A portion of the solution from Example B is spread over the dried film of Example C using a draw down blade with a fixed gap of 15 mils and is dried in the laboratory oven as before. A portion of the solution from Example C is spread on a glass plate using a draw down blade with a fixed gap of 5 mils and is dried in the laboratory oven as before. The resulting film is 3 mils (0.003 inches) in thickness and is comprised of three layers with a layer of opaque, red, flavored film on either side and a center layer of tobacco containing film. A 1.0 inch by 1.25 inch section of the film will typically disintegrate in the mouth in less than one minute.

Example F

Foamed Film

To a 100 gram portion of tobacco containing solution from Example B is added with vigorous mixing, 0.5 grams of sodium lauryl sulfate (a surface active agent). This solution is then mixed on a high shear mixer such as a Silverson Laboratory Homogenizer, Model L4RT-W, to create a uniform bubble structure. This highly aerated solution is then spread on a glass plate using a draw down blade with a fixed gap of 4 mils (0.040 inches) and is dried in a laboratory oven. The dry, foamed film has a thickness of 4 mils (0.004 inches) when it is removed from the glass plate. The weight of a section of this foamed film of 1.0 inch by 1.25 inch by 4 mils (0.004 inches) in thickness is 35% lower than an identical section of unfoamed film as prepared in Example B. The dissolution rate of the foamed film in the mouth is typically faster when compared to the identical unfoamed film as prepared in Example B.

Example G

Flakes

A solution is prepared in a beaker by adding 40 grams of spray dried Gum Arabic (TIC Gums, Inc.) and 0.4 grams of propylene glycol monostearate (PGMS) to 60 grams deionized water while mixing vigorously for 30 minutes. To 10 grams of this solution, 0.01 grams of FD&C Red No. 40 lake is added with high agitation to ensure uniform dispersion of the color. The solution is covered and set aside for 24 hours to permit all entrapped air to dissipate. A portion of this solution is then spread on a glass plate using a draw down blade with a fixed gap of 5 mils (0.005 inches). The glass plate is placed in a laboratory oven preset at 170° F. for 20 minutes until the film is thoroughly dried. When the film is removed from the glass plate, it breaks into many small pieces of high gloss, colorful, red flakes. This process is repeated with other FD&C lakes to produce flakes of many different colors. Flavors and artificial sweeteners can also be added to the flakes.

Example H

Tobacco Flakes

To 10 grams of the solution prepared in Example G is added 4 grams of finely ground tobacco powder. Films are prepared on glass plates and are dried, cooled, and removed in the same manner as in Example G. The resulting flakes are composed of 50% tobacco and 50% Gum Arabic and are a deep brown color. Flavors, if desired, can be added to the flakes. Materials such as sodium carbonate can also be added to the flakes to adjust pH.

Example I

Tobacco Film with Flakes

A film is prepared as in Example B. While the film is still wet on the glass plate, a measured quantity of flakes are prepared and are spread uniformly over the wet film. The glass plate is then dried in a laboratory oven; the film is cooled to room temperature and then removed from the glass plate. Typically, the dried film of Example B has a dry weight of 1 gram (containing 25% or 0.25 grams of tobacco). If this film is divided into 20 equal sections of film (1.0 inch by 1.25 inches by 2 mils), each section will weigh 50 milligrams (containing 25% or 12.5 milligrams of tobacco). If one gram of tobacco flakes (which are 50% by weight of tobacco) are spread uniformly over the film, the full piece of film will have a dry weight of 2 grams (containing a total of 0.75 grams of tobacco). When divided into 20 equal sections, each section will weigh 100 milligrams and will contain 37.5 milligrams of tobacco. The section of film cut into a 1.0 inch by 1.25 inch size will typically disintegrate in the mouth in less than one minute.

Example J

Tobacco Film with Decorative Flakes

The procedure outlined in Example I can be repeated using decorative flakes (e.g., colored flakes which do not contain any tobacco) or with blends of colored flakes and tobacco containing flakes. The resulting films have a colorful appearance.

Example K

Flavored Tobacco Film

TABLE K1

| | |
|---|---|
| HPMC | 36.56% |
| Starch | 12.18% |
| Tobacco | 24.37% |
| $Na_2CO_3$ | 1.46% |
| Plasticizer | 13.15% |
| Flavors | 6.82% |
| Sweetener | 0.49% |
| Surfactant | 0.97% |
| Water | 4.00% |

The following ingredients were weighed and combined in a container of suitable volume:

| MIX1 | |
|---|---|
| HM3PA2910 (Wolff Cellulosics) | 30.98 g |
| HM100PA2208 (Wolff Cellulosics) | 15.51 g |
| HM4000PA2910 (Wolff Cellulosics) | 2.60 g |
| B700 (Grain Processing Corporation) | 16.36 g |
| Tobacco Powder (average particle size < 80 μm) | 32.72 g |

The resultant mixture was mixed until homogeneous. In a separate container were weighed the following ingredients:

| MIX2 | |
|---|---|
| $Na_2CO_3$ | 1.96 g |
| Propylene Glycol Monostearate | 0.65 g |
| Sodium Lauryl Sulfate | 0.65 g |

In a third container were weighed the following ingredients:

| MIX3 | |
|---|---|
| Glycerin | 5.89 g |
| Propylene Glycol | 5.22 g |
| Polyethylene Glycol 400 | 6.54 g |
| Cinnamon Flavor | 6.54 g |
| Tobacco Flavor Modifier (Hagelin) | 2.62 g |
| Sucralose Solution 25% (Tate & Lyle) | 2.62 g |

A total of 619.14 g of boiling water was weighed into a stainless steel container. The water was stirred vigorously with an Arrow Model 1750 high shear mixer. To the water was added MIX2. Stirring was continued for 30 seconds, at which point MIX1 was added. Vigorous stirring was continued for 4 minutes. To the resultant solution was added MIX3. Vigorous stirring was continued for 1 minute. The resultant solution was transferred to a Silverson SS1 vessel, which had been adapted for mixing under vacuum. The vessel was attached to a Silverson L4RTU homogenizer motor unit. The solution was homogenized under vacuum (20-25 inches of Hg) for 2 minutes at 7500 RPM, after which an ice bath was placed around the homogenizer vessel. Homogenization continued under vacuum (20-25 inches of Hg) for 8 minutes at 10,000 RPM. After homogenization was complete, a portion of the solution was transferred to a 500-mL Nalgene bottle for storage.

A portion of the resultant gel solution was poured onto a glass plate that had previously been covered with an appropriately sized sheet of Mylar. The gel solution was drawn across the glass plate with a draw-down knife with a fixed gap of 15 mils. The glass plate was placed in a side-swept forced air oven (VWR model 1330FM), for 30 minutes, which had been set at 75° C. The resultant film, dried to approximately 4% moisture, was removed from the Mylar sheet and cut into appropriately sized units. A 1.0 inch by 1.25 inch unit of film disintegrated in the mouth in less than 30 seconds.

Relatively slower disintegrating films (e.g., films disintegrating in the mouth in greater than 30 seconds) were produced from the same solutions by casting the solution across the glass plate with a draw-down knife with a fixed gap of 30 mils. The films were dried in the same manner as above for 40 minutes. The films produced typically disintegrated in the mouth in less than 1 minute.

Super-fast disintegrating films (e.g., films disintegrating in the mouth in less than 15 seconds) were produced from the same solutions by foaming the solution prior to casting on the glass plate. Foaming was accomplished by subjecting 100 g of each solution to high shear mixing (with an Arrow Model 1750 high shear mixer) for approximately 3 minutes, after which the foamed solution was immediately cast on the glass plate with a draw-down knife with a fixed gap of 30 mils. The films produced typically disintegrated in the mouth in less than 15 seconds.

Example L

Flavored Tobacco Film

TABLE L1

| | |
|---|---|
| HPMC | 36.56% |
| Starch | 12.18% |
| Tobacco | 24.37% |
| Na$_2$CO$_3$ | 1.46% |
| Plasticizer | 10.71% |
| Flavors | 9.26% |
| Sweetener | 0.49% |
| Surfactant | 0.97% |
| Water | 4.00% |

The following ingredients were weighed and combined in a container of suitable volume:

| MIX1 | |
|---|---|
| HM3PA2910 (Wolff Cellulosics) | 30.98 g |
| HM100PA2208 (Wolff Cellulosics) | 15.51 g |
| HM4000PA2910 (Wolff Cellulosics) | 2.60 g |
| B700 (Grain Processing Corporation) | 16.36 g |
| Tobacco Powder (avg. particle size < 80 μm) | 32.72 g |

The resultant mixture was mixed until homogeneous. In a separate container were weighed the following ingredients:

| MIX2 | |
|---|---|
| Na$_2$CO$_3$ | 1.96 g |
| Propylene Glycol Monostearate | 0.65 g |
| Sodium Lauryl Sulfate | 0.65 g |

In a third container were weighed the following ingredients:

| MIX3 | |
|---|---|
| Glycerin | 4.58 g |
| Propylene Glycol | 5.22 g |
| Polyethylene Glycol 400 | 4.58 g |
| Mint Flavor | 9.81 g |
| Tobacco Flavor Modifier (Hagelin) | 2.62 g |
| Sucralose Solution 25% (Tate & Lyle) | 2.62 g |

A total of 619.14 g of boiling water was weighed into a stainless steel container. The water was stirred vigorously with an Arrow Model 1750 high shear mixer. To the water was added MIX2. Stirring was continued for 30 seconds, at which point MIX1 was added. Vigorous stirring was continued for 4 minutes. To the resultant solution was added MIX3. Vigorous stirring was continued for 1 minute. The resultant solution was transferred to a Silverson SS1 vessel, which had been adapted for mixing under vacuum. The vessel was attached to a Silverson L4RTU homogenizer motor unit. The solution was homogenized under vacuum (20-25 inches of Hg) for 2 minutes at 7500 RPM, after which an ice bath was placed around the homogenizer vessel. Homogenization continued under vacuum (20-25 inches of Hg) for 8 minutes at 10000 RPM. After homogenization was complete, a portion of the solution was transferred to a 500-mL Nalgene bottle for storage.

A portion of the resultant gel solution was poured onto a glass plate that had previously been covered with an appropriately sized sheet of Mylar. The gel solution was drawn across the glass plate with a draw-down knife with a fixed gap of 15 mils. The glass plate was placed in a side-swept forced air oven (VWR model 1330FM), for 30 minutes, which had been set at 75° C. The resultant film, dried to approximately 4% moisture, was removed from the Mylar sheet and cut into appropriately sized units. A 1.0 inch by 1.25 inch unit of film typically disintegrated in the mouth in 15-30 seconds.

Alternatively, the film includes wintergreen, spearmint, or apple flavor.

Relatively slower disintegrating films (e.g., films disintegrating in the mouth in greater than 30 seconds) and superfast disintegrating films (e.g., films disintegrating in the mouth in less than 15 seconds) were produced from the same solutions as described in Example K.

Example M

Peach Flavored Tobacco Film

TABLE M1

| | |
|---|---|
| HPMC | 29.12% |
| Starch | 9.71% |
| Tobacco | 19.41% |
| Na$_2$CO$_3$ | 1.16% |
| Plasticizer | 2.33% |
| Peach Puree | 29.66% |
| Flavors | 3.43% |
| Sweetener | 0.39% |
| Surfactant | 0.77% |
| Water | 4.00% |

The following ingredients were weighed and combined in a container of suitable volume:

| MIX1 | |
|---|---|
| HM3PA2910 (Wolff Cellulosics) | 30.98 g |
| HM100PA2208 (Wolff Cellulosics) | 15.51 g |
| HM4000PA2910 (Wolff Cellulosics) | 2.60 g |
| B700 (Grain Processing Corporation) | 16.36 g |
| Tobacco Powder (average particle size < 80 μm) | 32.72 g |

The resultant mixture was mixed until homogeneous. In a separate container were weighed the following ingredients:

| MIX2 | |
|---|---|
| Na$_2$CO$_3$ | 1.96 g |
| Propylene Glycol Monostearate | 0.65 g |
| Sodium Lauryl Sulfate | 0.65 g |

In a third container were weighed the following ingredients:

| MIX3 | |
| --- | --- |
| Glycerin | 1.31 g |
| Propylene Glycol | 1.31 g |
| Polyethylene Glycol 400 | 1.31 g |
| Peach Puree | 100.0 g |
| Peach Flavor | 3.27 g |
| Tobacco Flavor Modifier (Hagelin) | 2.62 g |
| Sucralose Solution 25% (Tate & Lyle) | 2.62 g |

A total of 619.14 g of boiling water was weighed into a stainless steel container. The water was stirred vigorously with an Arrow Model 1750 high shear mixer. To the water was added MIX2. Stirring was continued for 30 seconds, at which point MIX1 was added. Vigorous stirring was continued for 4 minutes. To the resultant solution was added MIX3. Vigorous stirring was continued for 1 minute. The resultant solution was transferred to a Silverson SS1 vessel, which had been adapted for mixing under vacuum. The vessel was attached to a Silverson L4RTU homogenizer motor unit. The solution was homogenized under vacuum (20-25 inches of Hg) for 2 minutes at 7500 RPM, after which an ice bath was placed around the homogenizer vessel. Homogenization continued under vacuum (20-25 inches of Hg) for 8 minutes at 10000 RPM. After homogenization was complete, a portion of the solution was transferred to a 500-mL Nalgene bottle for storage.

A portion of the resultant gel solution was poured onto a glass plate which had previously been covered with an appropriately sized sheet of Mylar. The gel solution was drawn across the glass plate with a draw-down knife with a fixed gap of 15 mils. The glass plate was placed in a side-swept forced air oven (VWR model 1330FM), for 30 minutes, which had been set at 75° C. The resultant film, dried to approximately 4% moisture, was removed from the Mylar sheet, and cut into appropriately sized units. A 1.0 inch by 1.25 inch unit of film typically disintegrated in the mouth in 15-30 seconds.

Relatively slower disintegrating films (e.g., films disintegrating in the mouth in greater than 30 seconds) and superfast disintegrating films (e.g., films disintegrating in the mouth in less than 15 seconds) were produced from the same solutions as described in Example K.

Example N

Flavored Tobacco Film for Sticks/Wraps/Pouches % Vacuum Forming

TABLE N1

| | |
| --- | --- |
| HPMC | 41.31% |
| Starch | 13.76% |
| Tobacco | 9.75% |
| Na$_2$CO$_3$ | 1.46% |
| Plasticizer | 18.99% |
| Flavors | 9.27% |
| Sweetener | 0.49% |
| Surfactant | 0.98% |
| Water | 4.00% |

The following ingredients were weighed and combined in a container of suitable volume:

| MIX1 | |
| --- | --- |
| HM3PA2910 (Wolff Cellulosics) | 38.48 g |
| HM100PA2208 (Wolff Cellulosics) | 19.27 g |
| HM4000PA2910 (Wolff Cellulosics) | 3.24 g |
| B700 (Grain Processing Corporation) | 20.32 g |
| Tobacco Powder (avg. particle size < 80 µm) | 14.39 g |

The resultant mixture was mixed until homogeneous. In a separate container were weighed the following ingredients:

| MIX2 | |
| --- | --- |
| Na$_2$CO$_3$ | 2.16 g |
| Propylene Glycol Monostearate | 0.72 g |
| Sodium Lauryl Sulfate | 0.72 g |

In a third container were weighed the following ingredients:

| MIX3 | |
| --- | --- |
| Glycerin | 7.19 g |
| Propylene Glycol | 7.19 g |
| Polyethylene Glycol 400 | 7.19 g |
| Triacetin | 6.47 g |
| Cinnamon Flavor | 10.80 g |
| Tobacco Flavor Modifier (Hagelin) | 2.88 g |
| Sucralose Solution 25% (Tate & Lyle) | 2.88 g |

A total of 606.10 g of boiling water was weighed into a stainless steel container. The water was stirred vigorously with an Arrow Model 1750 high shear mixer. To the water was added MIX2. Stirring was continued for 30 seconds, at which point MIX1 was added. Vigorous stirring was continued for 4 minutes. To the resultant solution was added MIX3. Vigorous stirring was continued for 1 minute. The resultant solution was transferred to a Silverson SS1 vessel, which had been adapted for mixing under vacuum. The vessel was attached to a Silverson L4RTU homogenizer motor unit. The solution was homogenized under vacuum (20-25 inches of Hg) for 2 minutes at 7500 RPM, after which an ice bath was placed around the homogenizer vessel. Homogenization continued under vacuum (20-25 inches of Hg) for 8 minutes at 10000 RPM. After homogenization was complete, a portion of the solution was transferred to a 500-mL Nalgene bottle for storage.

A portion of the resultant gel solution was poured onto a glass plate which had previously been covered with an appropriately sized sheet of Mylar. The gel solution was drawn across the glass plate with a draw-down knife with a fixed gap of 20 mils. The glass plate was placed in a side-swept forced air oven (VWR model 1330FM), for 35 minutes, which had been set at 75° C. The resultant film, dried to approximately 4% moisture, was removed from the Mylar sheet, and was stored in a plastic bag for future use.

Alternatively flavored tobacco films, e.g., apple flavored, were also produced following the preceding formulation and procedure.

Example O

Flavored/Colored Film for Sticks/Wraps/Pouches

TABLE O1

| | |
|---|---|
| HPMC | 41.31% |
| Starch | 13.76% |
| Fibersol-2 | 9.75% |
| $Na_2CO_3$ | 1.46% |
| Plasticizer | 18.99% |
| Flavors | 9.26% |
| Sweetener | 0.49% |
| Surfactant | 0.79% |
| Color | 0.20% |
| Water | 4.00% |

The following ingredients were weighed and combined in a container of suitable volume:

| MIX1 | |
|---|---|
| HM3PA2910 (Wolff Cellulosics) | 38.48 g |
| HM100PA2208 (Wolff Cellulosics) | 19.27 g |
| HM4000PA2910 (Wolff Cellulosics) | 3.24 g |
| B700 (Grain Processing Corporation) | 20.32 g |
| Fibersol-2 (Matsutani) | 14.39 g |
| FD&C Red 40 Alum Lake 35-42% (Sensient Colors) | 0.29 g |

The resultant mixture was mixed until homogeneous. In a separate container were weighed the following ingredients:

| MIX2 | |
|---|---|
| $Na_2CO_3$ | 2.16 g |
| Propylene Glycol Monostearate | 0.58 g |
| Sodium Lauryl Sulfate | 0.58 g |

In a third container were weighed the following ingredients:

| MIX3 | |
|---|---|
| Glycerin | 7.19 g |
| Propylene Glycol | 7.19 g |
| Polyethylene Glycol 400 | 7.19 g |
| Triacetin | 6.47 g |
| Cinnamon Flavor | 10.79 g |
| Tobacco Flavor Modifier (Hagelin) | 2.88 g |
| Sucralose Solution 25% (Tate & Lyle) | 2.88 g |

A total of 606.10 g of boiling water was weighed into a stainless steel container. The water was stirred vigorously with an Arrow Model 1750 high shear mixer. To the water was added MIX2. Stirring was continued for 30 seconds, at which point was added MIX1. Vigorous stirring was continued for 4 minutes. To the resultant solution was added MIX3. Vigorous stirring was continued for 1 minute. The resultant solution was transferred to a Silverson SS1 vessel, which had been adapted for mixing under vacuum. The vessel was attached to a Silverson L4RTU homogenizer motor unit. The solution was homogenized under vacuum (20-25 inches) for 2 minutes at 7500 RPM, after which an ice bath was placed around the homogenizer vessel. Homogenization continued under vacuum (20-25 inches) for 8 minutes at 10000 RPM. After homogenization was complete, a portion of the solution was transferred to a 500-mL Nalgene bottle for storage.

A portion of the resultant gel solution was poured onto a glass plate that had previously been covered with an appropriately sized sheet of Mylar. The gel solution was drawn across the glass plate with a draw-down knife with a fixed gap of 20 mils. The glass plate was placed in a side-swept forced air oven (VWR model 1330FM), for 35 minutes, which had been set at 75° C. Additional films were cast at 40 mils, and dried for 1 hour. The resultant films dried to approximately 4% moisture, were removed from the Mylar sheet, and were stored in a plastic bag for future use.

Alternatively flavors include mint flavor, wintergreen flavor, or spearmint flavor. Alternative colors include FD&C Blue Alum Lake 35-42%, FD&C Emerald Green Lake Blend, and FD&C Blue Alum Lake+FD&C Emerald Green Lake Blend.

Example P

Peach Flavored Film for Sticks/Wraps/Pouches

TABLE P1

| | |
|---|---|
| HPMC | 31.73% |
| Starch | 10.57% |
| Tobacco | 7.49% |
| $Na_2CO_3$ | 1.12% |
| Plasticizer | 14.59% |
| Peach Puree | 26.01% |
| Flavors | 3.37% |
| Sweetener | 0.37% |
| Surfactant | 0.75% |
| Water | 4.00% |

The following ingredients were weighed and combined in a container of suitable volume:

| MIX1 | |
|---|---|
| HM3PA2910 (Wolff Cellulosics) | 38.48 g |
| HM100PA2208 (Wolff Cellulosics) | 19.27 g |
| HM4000PA2910 (Wolff Cellulosics) | 3.24 g |
| B700 (Grain Processing Corporation) | 20.32 g |
| Tobacco Powder (average particle size < 80 μm) | 14.39 g |

The resultant mixture was mixed until homogeneous. In a separate container were weighed the following ingredients:

| MIX2 | |
|---|---|
| $Na_2CO_3$ | 2.16 g |
| Propylene Glycol Monostearate | 0.72 g |
| Sodium Lauryl Sulfate | 0.72 g |

In a third container were weighed the following ingredients:

| MIX3 | |
|---|---|
| Glycerin | 7.19 g |
| Propylene Glycol | 7.19 g |
| Polyethylene Glycol 400 | 7.19 g |
| Triacetin | 6.47 g |
| Peach Puree | 100.0 g |
| Peach Flavor | 3.60 g |
| Tobacco Flavor Modifier (Hagelin) | 2.88 g |
| Sucralose Solution 25% (Tate & Lyle) | 2.88 g |

A total of 606.10 g of boiling water was weighed into a stainless steel container. The water was stirred vigorously with an Arrow Model 1750 high shear mixer. To the water was added MIX2. Stirring was continued for 30 seconds, at which point was added MIX1. Vigorous stirring was continued for 4 minutes. To the resultant solution was added MIX3. Vigorous stirring was continued for 1 minute. The resultant solution was transferred to a Silverson SS1 vessel, which had been adapted for mixing under vacuum. The vessel was attached to a Silverson L4RTU homogenizer motor unit. The solution was homogenized under vacuum (20-25 inches of Hg) for 2 minutes at 7500 RPM, after which an ice bath was placed around the homogenizer vessel. Homogenization continued under vacuum (20-25 inches of Hg) for 8 minutes at 10000 RPM. After homogenization was complete, a portion of the solution was transferred to a 500-mL Nalgene bottle for storage.

A portion of the resultant gel solution was poured onto a glass plate that had previously been covered with an appropriately sized sheet of Mylar. The gel solution was drawn across the glass plate with a draw-down knife with a fixed gap of 20 mils. The glass plate was placed in a side-swept forced air oven (VWR model 1330FM), for 35 minutes, which had been set at 75° C. The resultant film, dried to approximately 4% moisture, was removed from the Mylar sheet, and was stored in a plastic bag for future use.

Example Q

Flavored/White Opaque Film for Coating

TABLE Q1

| | |
|---|---|
| HPMC | 45.46% |
| Starch | 15.15% |
| Fibersol-2 | 10.73% |
| Na$_2$CO$_3$ | 1.07% |
| Plasticizer | 10.73% |
| TiO$_2$ | 10.45% |
| Flavors | 1.07% |
| Sweetener | 0.27% |
| Surfactant | 1.07% |
| Water | 4.00% |

The following ingredients were weighed and combined in a container of suitable volume:

| MIX1 | |
|---|---|
| HM3PA2910 (Wolff Cellulosics) | 38.48 g |
| HM100PA2208 (Wolff Cellulosics) | 19.27 g |
| HM4000PA2910 (Wolff Cellulosics) | 3.24 g |
| B700 (Grain Processing Corporation) | 20.32 g |
| Fibersol-2 (Matsutani) | 14.39 g |

The resultant mixture was mixed until homogeneous. In a separate container were weighed the following ingredients:

| MIX2 | |
|---|---|
| Na$_2$CO$_3$ | 1.44 g |
| Propylene Glycol Monostearate | 0.72 g |
| Sodium Lauryl Sulfate | 0.72 g |

In a third container were weighed the following ingredients:

| MIX3 | |
|---|---|
| Glycerin | 3.60 g |
| Propylene Glycol | 3.60 g |
| Polyethylene Glycol 400 | 3.60 g |
| Triacetin | 3.60 g |
| TiO$_2$ suspension 50% (Sensient Colors) | 28.04 g |
| Tobacco Flavor Modifier (Hagelin) | 1.44 g |
| Sucralose Solution 25% (Tate & Lyle) | 1.44 g |

A total of 606.10 g of boiling water was weighed into a stainless steel container. The water was stirred vigorously with an Arrow Model 1750 high shear mixer. To the water was added MIX2. Stirring was continued for 30 seconds, at which point was added MIX1. Vigorous stirring was continued for 4 minutes. To the resultant solution was added MIX3. Vigorous stirring was continued for 1 minute. The resultant solution was transferred to a Silverson SS1 vessel, which had been adapted for mixing under vacuum. The vessel was attached to a Silverson L4RTU homogenizer motor unit. The solution was homogenized under vacuum (20-25 inches of Hg) for 2 minutes at 7500 RPM, after which an ice bath was placed around the homogenizer vessel. Homogenization continued under vacuum (20-25 inches of Hg) for 8 minutes at 10000 RPM. After homogenization was complete, a portion of the solution was transferred to a 500-mL Nalgene bottle for storage.

A portion of the resultant gel solution was poured onto a glass plate which had previously been covered with an appropriately sized sheet of Mylar. The gel solution was drawn across the glass plate with a draw-down knife with a fixed gap of 20 mils. The glass plate was placed in a side-swept forced air oven (VWR model 1330FM), for 35 minutes, which had been set at 75° C. The resultant film, dried to approximately 4% moisture, was removed from the Mylar sheet, and was stored in a plastic bag for future use.

Example R

Extruded Tobacco Films

TABLE R1

| | |
|---|---|
| Tobacco | 25.63% |
| Klucel LF | 61.53% |
| Na$_2$CO$_3$ | 3.32% |
| Plasticizer | 6.68% |
| Sweetener | 0.83% |
| Water | 2.00% |

The following ingredients were granulated in a manner similar to granulations utilized for tab production, as described herein, yielding a tobacco granulation with an approximate moisture of 4.50%:

| | |
|---|---|
| Klucel LF (Hercules/Aqualon) | 3448.0 g |
| Na$_2$CO$_3$ | 181.0 g |
| Sucralose (Tate & Lyle) | 45.0 g |
| Propylene Glycol | 363.0 g |
| Tobacco Powder (average particle size < 80 μm) | 1451.0 g |
| Water | 2344.0 g |

The tobacco granulation was introduced to the feed section of a Leistritz Micro-18 Twin Screw Extruder 40:1 L/D, which had been configured for co-rotating extrusion with a medium-shear screw design. Feed rates for the extrusion varied between 1-3 pounds per hour. Barrel zone temperatures varied between 75-240° F. Venting of volatiles from the extrusion melt was accomplished by incorporating a venting orifice prior to the discharge die of the extruder.

Tobacco film, with a width of approximately 3 inches and a thickness varying from 2-3 mils, was produced by incorporating a strip die at the discharge end of the extruder. Upon discharge, the tobacco film was calendared and cooled to room temperature by utilizing a 3-roll stacked chill roller. Downstream from the chill roller the film was taken up on a rewind reel, incorporating Mylar between the film layers to prevent adhesion. The tobacco film was placed in a container suitable for storage.

The tobacco film was subsequently used in the manufacture of dissolvable tobacco containing pouches, as described herein. The film disintegrated slowly in the mouth, over a period of 2-4 minutes.

Example S

Flavored Tobacco Film with Gelatin

TABLE S1

| | |
|---|---|
| HPMC | 35.95% |
| Gelatin | 0.98% |
| Starch | 12.30% |
| Tobacco | 23.64% |
| Na$_2$CO$_3$ | 1.47% |
| Plasticizer | 10.84% |
| Flavors | 9.35% |
| Sweetener | 0.50% |
| Surfactant | 0.97% |
| Water | 4.00% |

The following ingredients were weighed and combined in a container of suitable volume:

MIX1

| | |
|---|---|
| HM3PA2910 (Wolff Cellulosics) | 13.84 g |
| HM100PA2208 (Wolff Cellulosics) | 7.24 g |
| HM4000PA2910 (Wolff Cellulosics) | 1.21 g |
| B700 (Grain Processing Corporation) | 7.63 g |
| Gelatin | 0.61 g |
| Tobacco Powder (average particle size < 80 μm) | 15.27 g |

The resultant mixture was mixed until homogeneous. In a separate container were weighed the following ingredients:

MIX2

| | |
|---|---|
| Na$_2$CO$_3$ | 0.91 g |
| Propylene Glycol Monostearate | 0.30 g |
| Sodium Lauryl Sulfate | 0.30 g |

In a third container were weighed the following ingredients:

MIX3

| | |
|---|---|
| Glycerin | 2.14 g |
| Propylene Glycol | 2.44 g |
| Polyethylene Glycol 400 | 2.14 g |
| Mint Flavor | 4.58 g |
| Tobacco Flavor Modifier (Hagelin) | 1.22 g |
| Sucralose Solution 25% (Tate & Lyle) | 1.22 g |

A total of 288.93 g of boiling water was weighed into a stainless steel container. The water was stirred vigorously with an Arrow Model 1750 high shear mixer. To the water was added MIX2. Stirring was continued for 30 seconds, at which point was added MIX1. Vigorous stirring was continued for 4 minutes. To the resultant solution was added MIX3. Vigorous stirring was continued for 3 minutes. The resultant solution was transferred to a suitable container for storage.

A portion of the resultant gel solution was poured onto a glass plate which had previously been covered with an appropriately sized sheet of Mylar. The gel solution was drawn across the glass plate with a draw-down knife with a fixed gap of 20 mils. The glass plate was placed in a side-swept forced air oven (VWR model 1330FM), for 35 minutes, which had been set at 75° C. The resultant film dried to approximately 4% moisture, was removed from the Mylar sheet, and cut into appropriately sized units. A 1.0 inch by 1.25 inch unit of film dissolved in the mouth in less than 30 seconds, releasing flavor, sweetener, and tobacco.

Example T

Flavored Tobacco Film with Gelatin

TABLE T1

| | |
|---|---|
| HPMC | 32.01% |
| Gelatin | 4.92% |
| Starch | 12.30% |
| Tobacco | 23.64% |

TABLE T1-continued

| | |
|---|---|
| Na$_2$CO$_3$ | 1.47% |
| Plasticizer | 10.84% |
| Flavors | 9.35% |
| Sweetener | 0.50% |
| Surfactant | 0.97% |
| Water | 4.00% |

The following ingredients were weighed and combined in a container of suitable volume:

| MIX1 | |
|---|---|
| HM3PA2910 (Wolff Cellulosics) | 11.40 g |
| HM100PA2208 (Wolff Cellulosics) | 7.24 g |
| HM4000PA2910 (Wolff Cellulosics) | 1.21 g |
| B700 (Grain Processing Corporation) | 7.63 g |
| Gelatin | 3.05 g |
| Tobacco Powder (average particle size <80 μm) | 15.27 g |

The resultant mixture was mixed until homogeneous. In a separate container were weighed the following ingredients:

| MIX2 | |
|---|---|
| Na$_2$CO$_3$ | 0.91 g |
| Propylene Glycol Monostearate | 0.30 g |
| Sodium Lauryl Sulfate | 0.30 g |

In a third container were weighed the following ingredients:

| MIX3 | |
|---|---|
| Glycerin | 2.14 g |
| Propylene Glycol | 2.44 g |
| Polyethylene Glycol 400 | 2.14 g |
| Mint Flavor | 4.58 g |
| Tobacco Flavor Modifier (Hagelin) | 1.22 g |
| Sucralose Solution 25% (Tate & Lyle) | 1.22 g |

A total of 288.93 g of boiling water was weighed into a stainless steel container. The water was stirred vigorously with an Arrow Model 1750 high shear mixer. To the water was added MIX2. Stirring was continued for 30 seconds, at which point was added MIX1. Vigorous stirring was continued for 4 minutes. To the resultant solution was added MIX3. Vigorous stirring was continued for 3 minutes. The resultant solution was transferred to a suitable container for storage.

A portion of the resultant gel solution was poured onto a glass plate which had previously been covered with an appropriately sized sheet of Mylar. The gel solution was drawn across the glass plate with a draw-down knife with a fixed gap of 20 mils. The glass plate was placed in a side-swept forced air oven (VWR model 1330FM), for 35 minutes, which had been set at 75° C. The resultant film dried to approximately 4% moisture, was removed from the Mylar sheet, and cut into appropriately sized units. A 1.0 inch by 1.25 inch unit of film disintegrated in the mouth in less than 30 seconds, releasing flavor, sweetener, and tobacco.

Example U

Flavored Tobacco Film with Gelatin

TABLE U1

| | |
|---|---|
| HPMC | 27.09% |
| Gelatin | 9.85% |
| Starch | 12.30% |
| Tobacco | 23.64% |
| Na$_2$CO$_3$ | 1.47% |
| Plasticizer | 10.84% |
| Flavors | 9.35% |
| Sweetener | 0.50% |
| Surfactant | 0.97% |
| Water | 4.00% |

The following ingredients were weighed and combined in a container of suitable volume:

| MIX1 | |
|---|---|
| HM3PA2910 (Wolff Cellulosics) | 8.35 g |
| HM100PA2208 (Wolff Cellulosics) | 7.24 g |
| HM4000PA2910 (Wolff Cellulosics) | 1.21 g |
| B700 (Grain Processing Corporation) | 7.63 g |
| Gelatin | 6.11 g |
| Tobacco Powder (average particle size <80 μm) | 15.27 g |

The resultant mixture was mixed until homogeneous. In a separate container were weighed the following ingredients:

| MIX2 | |
|---|---|
| Na$_2$CO$_3$ | 0.91 g |
| Propylene Glycol Monostearate | 0.30 g |
| Sodium Lauryl Sulfate | 0.30 g |

In a third container were weighed the following ingredients:

| MIX3 | |
|---|---|
| Glycerin | 2.14 g |
| Propylene Glycol | 2.44 g |
| Polyethylene Glycol 400 | 2.14 g |
| Mint Flavor | 4.58 g |
| Tobacco Flavor Modifier (Hagelin) | 1.22 g |
| Sucralose Solution 25% (Tate & Lyle) | 1.22 g |

A total of 288.93 g of boiling water was weighed into a stainless steel container. The water was stirred vigorously with an Arrow Model 1750 high shear mixer. To the water was added MIX2. Stirring was continued for 30 seconds, at which point was added MIX1. Vigorous stirring was continued for 4 minutes. To the resultant solution was added MIX3. Vigorous stirring was continued for 3 minutes. The resultant solution was transferred to a suitable container for storage.

A portion of the resultant gel solution was poured onto a glass plate which had previously been covered with an appropriately sized sheet of Mylar. The gel solution was drawn across the glass plate with a draw-down knife with a fixed gap of 20 mils. The glass plate was placed in a side-swept forced air oven (VWR model 1330FM), for 35 minutes, which had been set at 75° C. The resultant film dried to approximately 4% moisture, was removed from the Mylar sheet, and cut into appropriately sized units. A 1.0 inch by 1.25 inch unit of film disintegrated in the mouth in less than 30 seconds, releasing flavor, sweetener, and tobacco.

Tabs.

Compositions of the invention may also be produced as tabs, such as super fast disintegrate (about 15 seconds), fast disintegrate (less than 2 minutes), slow disintegrate (2-10 minutes), and chewable tabs.

Tabs may be sized as individual servings or smaller, a plurality of which constitute an individual serving. Tabs sized as individual servings typically have dimensions of 5 mm to 15 mm. Smaller tabs typically range from 2 to 4 mm in diameter. Such smaller tabs may be fabricated in a variety of colors or flavors, e.g., for simultaneous consumption. Tabs may be shaped as a wafer, a convex or concave pellet, ovals, or any other shape known to the trade. Tabs may also be foamed to provide faster dissolution or disintegration in the mouth. Tabs may also be layered to provide a variety of tastes or mouth feels as the tab dissolves or disintegrates. Tabs may also be coated to modify color or taste or to provide mechanical strength for improved handling. In one embodiment, a tab designed to disintegrate rapidly in water may be coated with a very thin water insoluble coating to provide protection to the tab while a second, water soluble coating is applied.

Tabs may be fabricated from a dry mix, known as direct compression or from pregranulated materials by any forming method known in the art, e.g., via a press, injection molding, compression molding, injection foam molding, or compression foam molding.

Tab Examples

The following table shows exemplary ingredients for fabricating tabs of the invention.

TABLE V1

| | Exemplary Range (%) | Ex. V Fast (%) | Ex. W Fast (%) | Ex. X Slow (%) | Ex. Y Slow (%) |
|---|---|---|---|---|---|
| Water soluble polymer | 0-70 | 0 | 3 | 23 | 0 |
| Tobacco | 1-70 | 27 | 20 | 27 | 30 |
| Flavor Oil | 0.5-4.0 | 2 | 1.8 | 2 | 2 |
| Artificial Sweetener | 0.05-0.4 | 0.15 | 0.15 | 0.15 | 0.1 |
| Sugar | 1-80 | 64 | 35 | 45.85 | 33.3 |
| Maltodextrin | 0-50 | 0 | 19 | 0 | 0 |
| Disintegrant | 0.1-15 | 6.35 | 3.0 | — | — |
| Starch | 5-80 | 0 | 17.35 | — | 50 |
| Release Agent | 0.1-2.0 | 0.5 | 0.5 | 0.5 | 0.5 |
| Emulsifier | 0.1-5.0 | 0 | 0.2 | 0.5 | 0.1 |

Example Z

Exemplary Chewable Tab

A chewable tab can be formed using the following ingredients: compressible sugar (40%); tobacco (20%); dextrose (25%); maltodextrin (13%); coloring agents (0.05%); flavor (1.35%); and magnesium stearate (0.60%).

Example AA

Thermoplastic Tab

A thermoplastic tab can be formed using the following ingredients (in parts): hydroxypropyl cellulose (HPC) 54; tobacco 27; microcrystalline cellulose 10; propylene glycol 4; artificial sweetener 2; flavor 2; and stabilizer 0.2. The ingredients are dry mixed and fed to an extruder using barrel temperatures necessary to melt the HPC (typically 340-370° F.). A rod of about ½ inch diameter is extruded and cut to size sufficient to form a tab.

Example AB

Tobacco Tab

TABLE AB1

Formulation of Tobacco Tab

| Ingredients | % Dry Weight Basis |
|---|---|
| Tobacco Powder | 25.00 |
| Sweetener | 32.11 |
| Maltodextrin | 40.22 |
| Flavors | 0.75 |
| Emulsifier | 1.36 |
| $Na_2CO_3$ | 0.56 |
| Total | 100.00 |

TABLE AB2

Formulation of Binding Solution for Production of Tobacco Tab

| Ingredients | Percent |
|---|---|
| Water | 45.00 |
| Maltodextrin | 53.05 |
| Emulsifier | 1.80 |
| Sweetener | 0.15 |
| Total | 100.00 |

Preparation of Binding Solution

Ingredient amounts, as noted in Table AB2, were weighed out into separate containers. Gum Arabic Pre-hydrated (emulsifier) was slowly added to the water and mixed under high shear agitation in a stainless steel vessel. After complete dissolution, M 585 maltodextrin (Grain Processing Corporation) was added slowly to the water. Once M 585 was completely dissolved, the Sucralose sweetener (Tate & Lyle) was added slowly and mixed thoroughly to ensure complete dissolution.

Formulary amounts of peppermint and spearmint flavors and $Na_2CO_3$ as noted in Table AB1 were added to the binding solution. The entire mixture was homogenized for approximately 20 minutes at 9000-10000 RPMs with the aid of a homogenizer. The proper amount of binding solution to use was determined by the batch size and the ingredient percentages shown in Table AB1. The homogenized solution was transferred into the flavor holding/pumping tank.

Preparation of Dry Ingredients

The formulary amounts of mannitol (sweetener) and tobacco powder (bone dry basis), as noted in Table AB1, were blended together and placed in the product bowl.

Preparation of Vector Multiflo-15 Fluid Bed Chamber

A Vector Multiflo-15 fluid bed coater was used to apply the binding solution to the dry ingredient blend to form the final granulation. The manual process was selected on the control panel computer. The machine operating parameters, located in Table AB3, were loaded into the program:

TABLE AB3

Vector Multiflo-15 Fluid Bed

| Parameter | Settings |
|---|---|
| Inlet Temperature (Celsius) | 60 |
| Airflow (CFM) | 150 |
| Flowrate (G/Min) | 125 |
| Filter Pulse Interval (Sec) | 30 |
| Post-Pulse Time (Sec) | 60 |

The appropriate amount of binding solution to be sprayed on was also loaded into the program. The binding solution amount was determined by the desired batch size to achieve the ingredient percentages shown in Table AB1.

Granulation Process

Once the dry ingredients were fluidized in the fluid bed chamber and achieved a temperature of 40-45° C., the binding solution was slowly sprayed onto the dry ingredients to form the granulation. The nozzle pressure was set at 22 psi and airflow at 200 CFM. The airflow was increased to ensure good product movement or fluidization in the fluid bed chamber. Once all the binding solution had been applied, the airflow was reduced to 200 CFM. The process was stopped once the product temperature reached approximately 43° C.

Preparation of Granulation for Forming Tabs

The granulated material was then sized through a 12-mesh screen. The magnesium stearate (lubricant) was sized through a 40-mesh screen. The formulary amount of magnesium stearate as noted in Table AB4 was combined with the granulated material in a plastic bag and manually shaken for 2 minutes.

TABLE AB4

Formulation of Ingredients for Forming Tabs

| Ingredients | % Dry Weight Basis |
|---|---|
| Granulated Material | 99.50 |
| Lubricant | 0.50 |
| Total | 100.00 |

Tab Forming Process

The granulated material plus lubricant was loaded into the hopper of the press. The following parameters noted in Table AB5 were set on the Vanguard VSP 8 Mini Rotary Press:

TABLE AB5

Parameters for Tobacco Tab

| Parameters | Fast Disintegrate | | Slow Disintegrate | |
|---|---|---|---|---|
| | Settings | Ranges | Settings | Ranges |
| Fill Depth (MM) | 8.0 | | 11.3 | 11.3-11.4 |
| Thickness (MM) | 1.3 | | 1.8 | |
| Principal Pressure (KN) | 5.0 | | | 10.8-12.0 |
| Ejection Pressure (MM) | | | | 0.03-0.12 |

Fast disintegrate disintegrated in the mouth within 1 to 3 minutes. Slow disintegrate disintegrated in the mouth between 5-8 minutes.

Example AC

Tobacco Tab

TABLE AC1

Formulation of Tobacco Tab

| Ingredients | % Dry Weight Basis |
|---|---|
| Tobacco Powder | 25.00 |
| Sweetener | 34.11 |
| Maltodextrin | 38.58 |
| Flavors | 1.00 |
| Emulsifier | 1.31 |
| Total | 100.00 |

TABLE AC2

Formulation of Binding Solution for Production of Tobacco Tab

| Ingredients | Percent |
|---|---|
| Water | 45.00 |
| Maltodextrin | 53.04 |
| Emulsifier | 1.80 |
| Sweetener | 0.16 |
| Total | 100.00 |

The procedures previously stated in Example AB1 for binding solution preparation were followed. Formulary amounts of peppermint and spearmint flavors as noted in Table AC1 and 45.00 grams of $Na_2CO_3$ were added to binding solution. The remaining procedures for the make-up for the binding solution, preparation of dry ingredients, preparation of Vector Multiflo-15 Fluid Bed Chamber, and granulation process were followed.

Preparation of Granulation for Forming Tabs

The granulated material and magnesium stearate were sized through the appropriate screens as previously stated. The formulary amount of magnesium stearate (0.75% for a fast disintegrate or 1.00% for a slow disintegrate) was combined with the granulated material in a plastic bag and manually shaken for 2 minutes.

Tab Forming Process

The machine operating parameters noted in Table AC3 were set on the Vanguard

TABLE AC3

Tab Forming Parameters for Tobacco Tab

| Parameters | Fast Disintegrate | | Slow Disintegrate | |
|---|---|---|---|---|
| | Settings | Ranges | Settings | Ranges |
| Fill Depth (MM) | 6.8 | | 9.9 | |
| Thickness (MM) | 1.1 | | | 2.0-2.1 |
| Principal Pressure (KN) | | 6.9-7.2 | | 3.8-4.0 |
| Ejection Pressure (MM) | | | | 0.03-0.15 |

Example AD

Tobacco Tab

TABLE AD1

Formulation of Tobacco Tab

| Ingredients % | Dry Weight Basis |
|---|---|
| Tobacco Powder | 25.00 |
| Filler | 30.00 |
| Maltodextrin | 42.15 |
| Flavor | 0.75 |
| Emulsifier | 1.43 |
| Sweetener | 0.12 |
| $Na_2CO_3$ | 0.56 |
| Total | 100 |

TABLE AD2

Formulation of Binding Solution for Production of Tobacco Tab

| Ingredients | Percent |
|---|---|
| Water | 45.00 |
| Maltodextrin | 53.06 |
| Emulsifier | 1.80 |
| Sweetener | 0.14 |
| Total | 100.00 |

The procedures previously stated for binding solution preparation were followed. Formulary amounts of Cinnamon Flavor and $Na_2CO_3$ as noted in Table AD1, were added to the binding solution. The remaining procedures for the make-up of the binding solution, preparation of dry ingredients (lactose filler combined with tobacco powder), preparation of the Vector Multiflo-15 Fluid Bed Chamber, and the granulation process were followed.

Preparation of Granulation for Forming Tabs

The granulated material and magnesium stearate were sized through 12- and 40-mesh screens, respectively. The formulary amount of magnesium stearate (0.50% for a fast disintegrate or 1.00% for a slow disintegrate) was combined with the granulated material in a plastic bag and manually shaken for 2 minutes.

Tab Forming Process

The parameters noted in Table AD3 were set on the Vanguard VSP 8 Mini Rotary Press:

TABLE AD3

Tab Forming Parameters for Tobacco Tab

| Parameters | Fast Disintegrate | | Slow Disintegrate | |
|---|---|---|---|---|
| | Settings | Ranges | Settings | Ranges |
| Fill Depth (MM) | 7.7 | | 11.2 | 11.2-11.3 |
| Thickness (MM) | 1.1 | | 1.7 | 1.7-1.8 |
| Principal Pressure (KN) | | 5.7-6.0 | | 3.8-4.0 |
| Ejection Pressure (MM) | | 0.03-0.08 | | 0.03-0.17 |

Example AE

Tobacco Tab

The same procedures were followed for making a Tobacco Tab in Example AD except wintergreen flavor was used in place of cinnamon flavor.

Preparation of Granulation for Forming Tabs

The finished material was then sized through a 12-mesh screen. The magnesium stearate was sized through a 40-mesh screen. The formulary amount of magnesium stearate (0.50% for a fast disintegrate or 0.75% for a slow disintegrate) was combined with the granulated material in a plastic bag and manually shaken for 2 minutes.

Tab Forming Process for Tobacco Tab

The parameters noted in Table AE1 were set on the Vanguard VSP 8 Mini Rotary Press:

TABLE AE1

Tab Forming Parameters for Tobacco Tab

| Parameters | Fast Disintegrate | | Slow Disintegrate | |
|---|---|---|---|---|
| | Settings | Ranges | Settings | Ranges |
| Fill Depth (MM) | 8.1 | | 12.0 | 12.0-12.1 |
| Thickness (MM) | 1.1 | 1.1-1.2 | 1.8 | |
| Principal Pressure (KN) | 5.7 | 5.7-6.0 | 4.5 | 4.5-5.2 |
| Ejection Pressure (MM) | | 0.03-0.09 | | 0.04-0.19 |

Example AF

Tobacco Tab with an Opaque, White Coating

TABLE AF1

Formulation of Tobacco Tab

| Ingredients | % Dry Weight Basis |
|---|---|
| Tobacco | 25.00 |
| Filler | 30.00 |
| Maltodextrin | 39.74 |
| Flavor | 0.75 |
| Emulsifier | 1.35 |
| Sweetener | 0.10 |
| $Na_2CO_3$ | 0.56 |
| Tobacco Flavor Modifier | 2.50 |
| Total | 100 |

TABLE AF2

Formulation of Binding Solution for Production of Tobacco Tab

| Ingredients | Percent |
|---|---|
| Water | 45.00 |
| Maltodextrin | 53.07 |
| Emulsifier | 1.80 |
| Sweetener | 0.13 |
| Total | 100 |

Preparation of Binding Solution

The procedures previously stated for binding solution preparation were followed. Formulary amounts of apple flavor, natural bitter blocker (Comax), and $Na_2CO_3$ as noted in Table AF1 were added to binding solution. The remaining procedures for the make-up of the binding solution, preparation of dry ingredients (lactose filler plus tobacco powder), preparation of the Vector Multiflo-15 Fluid Bed Chamber, and the granulation process were followed.

Preparation of Granulation for Tab Forming

The finished material was then sized through a 12-mesh screen. The magnesium stearate was sized through a 40-mesh screen. The formulary amount of magnesium stearate (0.75% for a slow disintegrate) was combined with the granulated material in a plastic bag and manually shaken for 2 minutes.

Tab Forming Process

The parameters noted in Table AF3 were set on the Vanguard VSP 8 Mini Rotary Press:

TABLE AF3

Tab Forming Parameters for a Slow Disintegrate Tobacco Tab

| Parameters | Settings | Ranges |
| --- | --- | --- |
| Fill Depth (MM) | 13.6 | 13.5-13.7 |
| Thickness (MM) | 2.4 | 2.4-2.5 |
| Principal Pressure (KN) | | 4.5-5.2 |
| Ejection Pressure (MM) | | 0.04-0.24 |

Tobacco Tab Coating-Suspension Makeup

A 20% Opadry II aqueous solution was prepared as directed by the manufacturer and allowed to mix 45 minutes prior to coating.

Coating Process

Tabs (5.5-6.5 KG) were placed in the coating pan of a Vector/Freund Hi-Coater pan coating machine and warmed until the exhaust temperature reached 45° C. This was done with the pan running at less than 5 RPMs to minimize Tab attrition. Air at 75° C. and 100 CFM ran across the pan at a pan pressure of −0.5" water.

Once the tabs reached temperature, the pan speed was increased to approximately 15 RPMs and the Opadry coating suspension was applied at a rate of 15-20 grams/minute. The suspension was continually mixed during application to prevent the solids from settling. The spray was atomized with approximately 100 liters of air per minute at approximately 70 psi. The atomized spray was formed into a pattern using directional air ports on the nozzle set at approximately 50 liters of air per minute at approximately 70 psi.

Inlet air temperature was periodically increased or decreased to maintain an exhaust temperature between 43 and 46° C.

Spraying was continued until desired amount of solids was applied to satisfy formulary requirements which was typically around 3%, or until tabs were visually satisfactory.

Example AG

Tobacco Solid Disintegratable

The following ingredients were weighed out into individual containers:

| | |
| --- | --- |
| Klucel EF (Hercules) | 60 g |
| Tobacco Powder | 75 g |
| Tobacco Flavor Modifier | 6 g |
| Corn Syrup (65%) | 45 g |
| Sucrose | 45 g |
| B700 (Grain Processing Corp.) | 51 g |
| Sucralose Solution 25% (Tate & Lyle) | 3 g |
| Propylene Glycol | 3 g |

-continued

| | |
| --- | --- |
| Sodium Carbonate | 1.5 g |
| Water | 6 g |
| Oil of Peppermint | 4.5 g |
| Water portion 1 (hot) | 120 g |
| Water portion 2 (cold) | 120 g |

The 6 g of water was added to the sodium carbonate, and the mixture was stirred. This mixture was allowed to stir until it was added to the other ingredients later in the process.

Water portion 2 (cold) was placed in an ice bath to chill while water portion 1 (hot) was heated to 60° C. and transferred to a stainless steel container. The 60° C. water was stirred with an Arrow Model 1750 high shear mixer and the Klucel EF gradually added to the water. This solution was stirred for several minutes. Water portion 2 (cold) was then added to the mixture. An ice bath was placed under the stainless steel container, and the mixture was stirred for 15 minutes.

After 15 minutes of stirring, the remaining ingredients were added to the mixture one at a time. The mixture was thoroughly blended prior to the addition of the next ingredient. The ingredients were added in the following order: tobacco flavor modifier, propylene glycol, sucralose solution, corn syrup, sodium carbonate solution, sucrose, tobacco powder, B700, and oil of peppermint. Ice was added to the ice bath throughout the mixing process to keep the mixture cold. After all ingredients were added, the mixture was stirred for an additional 10 minutes.

The container was removed from the ice bath and the mixture was dispensed in solid disintegratable portions onto wax paper and allowed to dry at room temperature for 24 hours. The solid disintegratables were removed from the wax paper and transferred to another sheet of wax paper to continue drying at room temperature. The desired hardness for the solid disintegratables was achieved after 12 to 24 hours of continued drying.

Example AH

Tobacco Solid Disintegratable

The following ingredients were weighed out into individual containers:

| | |
| --- | --- |
| HPMC 2910 HM E5/6 Bv (Celanese) | 60 g |
| Tobacco Powder | 75 g |
| Tobacco Flavor Modifier | 6 g |
| Corn Syrup (65%) | 45 g |
| Sucrose | 45 g |
| B700 (Grain Processing Corp.) | 39 g |
| Sucralose Solution 25% (Tate & Lyle) | 3 g |
| Propylene Glycol | 15 g |
| Sodium Carbonate | 1.5 g |
| Water | 6 g |
| Oil of Peppermint | 4.5 g |
| Water portion 1 (hot) | 120 g |
| Water portion 2 (room temp.) | 120 g |

The 6 g of water was added to the sodium carbonate, and the mixture was stirred. This mixture was allowed to stir until it was added to the other ingredients later in the process.

Water portion 1 (hot) was heated to 80° C. and transferred to a stainless steel container. The 80° C. water was stirred with an Arrow Model 1750 high shear mixer, and the HPMC gradually added to the water. This solution was stirred for several minutes. Water portion 2 (room temp.) was then added to the mixture, and the mixture was stirred for 15 minutes.

After 15 minutes of stirring, the remaining ingredients were added to the mixture one at a time. The mixture was thoroughly blended prior to the addition of the next ingredient. The ingredients were added in the following order: tobacco flavor modifier, propylene glycol, sucralose solution, corn syrup, sodium carbonate solution, sucrose, tobacco powder, B700, and oil of peppermint. After all ingredients were added, the mixture was stirred for an additional 10 minutes.

The mixture was dispensed in portions onto wax paper and allowed to dry at room temperature for 24 hours. The solid disintegratables were removed from the wax paper and transferred to another sheet of wax paper to continue drying at room temperature. The desired hardness for the solid disintegratables was achieved after 12 to 24 hours of continued drying.

A similar product was made using the same formulation, mixing process, and dispensing process, but the solid disintegratables were dried in a forced air oven (VWR Model 1330FM) set at 32° C. for one hour. The solid disintegratables were then removed from the oven and dried at room temperature for 24 hours. Additionally, solid disintegratables were dried in the forced air oven at 32° C. for 18 hours. A slightly harder solid disintegratable with a dull finish was achieved with this drying technique.

Example AI

Multilayer Tab

Commercially available press equipment can be used to prepare tabs with two or more distinct layers. The composition of these layers can be the same or different in composition. Individual layers can be differentiated by color, flavor, tobacco type, tobacco content, dissolution rate, and other similar characteristics. For example, one layer could disintegrate very rapidly to release flavor or flavor masking ingredients. A second layer containing tobacco powder could disintegrate more slowly thereby gradually exposing the tobacco.

Shaped Parts.

Tobacco compositions may also be formed into products that are sufficiently rigid to be easily handled. These shaped products may vary in physical properties and range from highly flexible to highly stiff parts. Such products may be formed into any shape and be dense or foamed. These compositions typically have a moisture content of 2-50%, preferably 5-10%, of the finished part weight. Exemplary shapes include a tube, a toothpick, a stick, a twist, or a solid rod. Typically, a shaped part will be sucked or chewed on for an extended period of time to release tobacco organoleptic components into the mouth. A shaped part may or may not disintegrate orally. Parts that disintegrate may do so over a period of 1-60 minutes, preferably from 1-10 minutes.

Shaped parts may or may not be sized to fit entirely in the mouth. Compositions larger than the mouth may be partially inserted. Typically the largest dimension of a shaped part is 6 inches, more preferably 2.5 inches.

Shaped parts may contain discrete regions, e.g., with each region having the same or different flavor or color or size or form of tobacco, e.g., tobacco perceived as soluble. For example, a twist may contain individual strands, each having a different flavor or color or size or form of tobacco. As further examples, shaped parts may be prepared in multistep processes in which molded or extruded parts are composed of layers, two or more of which contain different flavors, colors, or sizes or forms of tobacco.

Shaped part compositions may be fabricated by any method known in the art, e.g., extrusion, compression molding, injection molding, impact forming, foam molding, blow molding, and overmolding. In addition, shaped parts may be based on water soluble or thermoplastic formats. In one embodiment, an aqueous-based shaped part is fabricated by forming a viscous paste (e.g., via Hobart process) of the format, water, tobacco, and other ingredients and pressing the paste into a form, extruding through a die, or forming a sheet from which shapes are cut. The cut or formed part may then be dried to the desired moisture level of from 2-50%, preferably from 5-10% of the finished part weight for very rigid parts and from 10-50% for highly flexible parts. In another embodiment, the aqueous paste can be formed in a two stage extrusion process (e.g., via a Wenger twin screw extruder) in which the format, water, tobacco, and other ingredients are blended in a mixing or pre-extrusion stage of the machine, and the resulting paste is fed directly to the twin screw extrusion element of the machine and is extruded through a die to form a shape, which is then dried to the desired moisture level. A thermoplastic-based shaped part is fabricated, for example, by mixing components via a PK blender, high intensity mixer, pre-pelletizer, or granulation (fluid bed or Hobart) process. The mixed components may then be extruded through conventional single or twin screw extruders to form shaped parts or the mixture can be fed into injection molding machines or other thermoplastic processing machinery to form shaped parts.

Shaped Part Examples

Example AJ

Injection Molded Shaped Parts

The following table provides exemplary shaped parts to be formed by injection molding.

TABLE AJ1

| Ingredient | 1 % | 2 % | 3 % | 4 % | 5 % | 6 % | 7 % | 8 % |
|---|---|---|---|---|---|---|---|---|
| Tobacco | 47.98 | 45.59 | 67.18 | 63.83 | 78.22 | 74.32 | 29.33 | 27.87 |
| Low viscosity HPC | 48.02 | 45.62 | 28.84 | 27.40 | 19.59 | 18.61 | 68.48 | 65.06 |
| Water | 4 | 3.80 | 3.98 | 3.78 | 2.19 | 2.08 | 2.19 | 2.08 |
| Propylene glycol | | 4.99 | | 4.99 | | 4.99 | | 4.99 |

Heating zones were Zone 1—300-340° F.; Zone 2—350-370° F.; Zone 3—300-340° F.; mold temperature was ambient. Sufficient composition was fed to the screw to equal one injection cycle; the material was immediately injected into the mold; the mold was opened after 10 seconds; and the part was removed. The shaped part was a stepped color chip, 2 inches by 3 inches by steps at $1/8^{th}$, $1/4^{th}$, and $3/8^{th}$ inch thickness.

Example AK

Compression Molded Shaped Parts

The following table provides exemplary shaped parts formed by compression molding.

TABLE AK1

| Ingredient | A % | B % | C % | D % | E % | F % | G % |
|---|---|---|---|---|---|---|---|
| Tobacco | 26.47 | 25.00 | 25.00 | 30.00 | 25.00 | 25.00 | 25.00 |
| Corn starch | 49.41 | 30.30 | | 9.50 | 60.60 | 30.30 | 56.60 |
| Starch B-820 | | | 30.30 | | | | |
| Maltodextrin | | | | | | 30.30 | |
| Low viscosity HPC | | | | 45.00 | | | |
| Soluble fiber | | 30.30 | 30.30 | | | | |
| Cinnamon | 4.41 | 5.00 | 5.00 | 5.00 | 5.00 | 5.00 | 5.00 |
| Flavor oil | 4.41 | 5.00 | 5.00 | 5.00 | 5.00 | 5.00 | 5.00 |
| Sucralose | 0.88 | 0.90 | 0.90 | 0.90 | 0.90 | 0.90 | 0.90 |
| Sodium carbonate | 2.65 | 2.50 | 2.50 | 2.50 | 2.50 | 2.50 | 2.50 |
| Glycerin | | 1.00 | 1.00 | 2.00 | 1.00 | 1.00 | 5.00 |
| Propylene glycol | 11.77 | | | | | | |

10-50 grams of water is added per 100 grams of dry compound—sufficient to soften the mix and enable it to pass through a pasta die mounted on a mixer. The mold parameters are as follows:

TABLE AK2

| | |
|---|---|
| Mold Temperature | 220-280° F. |
| Residence Time | 5 seconds to 60 seconds |
| Toothpick mold cavity | $5/32$nds inch diameter by $2^{3/8 th}$ length |
| Stick mold cavity | $3/8^{th}$ inch diameter by $2^{3/8 th}$ length |
| Disc mold cavity | $3/4$ inch diameter by $1/4$ inch depth |

Longer residence times produced more rigid parts, as long as the steam was allowed to freely vent during the expansion of the part. Additives may also be employed so that the shaped part remains flexible after removal from the tool. The parts containing a majority of low viscosity HPC formed excellent pieces if left in the tool for an extended time (40 to 60 seconds). The inclusion of plasticizer increased the rate of moisture absorption from the atmosphere, which caused some parts to soften over time.

When the mold cavities were completely filled with molding compound, dense and rigid parts were prepared. When the mold cavities were filled to about 75% of the mold capacity, the compound expanded under the pressure of expanding steam to form foamed parts which had good rigidity, good flavor, and which disintegrated readily in the mouth.

Foaming can be accomplished in aqueous systems by incorporating a surface active agent (e.g., sodium lauryl sulfate) into the mix and beating to incorporate air; foaming or aeration can also be achieved by introducing a gas (e.g. nitrogen) to the aqueous system while the composition is under high shear. The aqueous system is then dried to the desired moisture level to create a stable foamed composition. In one embodiment, an aqueous composition is introduced to partially fill a compression mold; the mold is closed; the mold temperature is raised above the boiling point of water to form steam, which expands the aqueous composition to fill the void area and to create a foamed, shaped part. For thermoplastic systems, foaming can be accomplished by incorporating water into the tobacco/format composition; the temperature is raised to above the boiling point of water to form steam; and, as the tobacco composition exits a die, the steam expands to create a foamed structure. In another embodiment, gas (e.g., nitrogen or carbon dioxide) is introduced into the molten, thermoplastic, tobacco composition prior to its discharge from an extruder resulting in a highly uniform foam structure in the shaped tobacco composition. Other thermoplastic foaming processes well known in the art (e.g., injection foam molding) can be used to create foamed, tobacco compositions and shaped parts.

Example AL

Exemplary Aqueous Shaped Parts

Tables AL1 and AL2 show exemplary ingredients for fabricating aqueous shaped parts of the invention. Sufficient water is added to form a viscous paste.

TABLE AL1

| | Exemplary (parts) | Preferred | Example |
|---|---|---|---|
| Tobacco | 1-80 | 30-50 | 54 |
| Flavor | 0.5-4 | 2.5-3 | 3 |
| Insoluble Fiber | 4.5-36 | 22.5-27 | 27 |
| Water Soluble Polymer | 1-50 | 5-20 | 10 CMC 7MF (medium viscosity) |
| Filler/Disintegrant | 1-50 | 10-30 | 30 microcrystalline cellulose |
| Artificial Sweetener | 0.05-5 | 0.1-2 | 0.2 Sucralose |
| Dispersant | 0.1-20 | 0.1-2 | 0.2 Sodium Lauryl Sulfate |

TABLE AL2

| | Exemplary (parts) | Preferred | Example |
|---|---|---|---|
| Tobacco | 1-80 | 20-50 | 27 |
| Flavor | 0.5-4 | 1-3 | 1 |
| Insoluble Fiber | 4.5-36 | 9-27 | 9 |
| Water Soluble Polymer | 1-50 | 5-25 | 18 low viscosity HPC |
| Filler/Disintegrant | 1-50 | 10-30 | 10 microcrystalline cellulose |
| Artificial Sweetener | 0.05-3 | 0.1-1 | 0.5 Sucralose |
| Dispersant | 0.1-20 | 0.1-2 | 0.2 sodium lauryl sulfate |

Example AM

Exemplary Thermoplastic Shaped Parts

Table AM1 shows exemplary ingredients for fabricating thermoplastic shaped parts of the invention.

TABLE AM1

| | Exemplary (parts) | Preferred | 1 | 2 | 3 |
|---|---|---|---|---|---|
| Tobacco | 10-80 | 25-80 | 76.6 | 50 | 25 |
| Plasticizer | 1-20 | 1-20 | 3 propylene glycol | 4.6 propylene glycol | 5.6 propylene glycol |

TABLE AM1-continued

|  | Exemplary (parts) | Preferred | 1 | 2 | 3 |
|---|---|---|---|---|---|
| Water Soluble Polymer | 10-80 | 20-50 | 20 | 30 | 40 |
| Filler | 0-60 | 0-30 | — | 15 | 29 |
| Stabilizer | 0.1-0.5 | 0.2-0.4 | 0.4 | 0.4 | 0.4 |

Example AN

Tobacco Rods

A tobacco rod is made from tobacco (54 parts); flavor (2); insoluble fiber (28); CMC (10); artificial sweetener (0.2); and microcrystalline cellulose (30). Water sufficient to form a viscous paste (e.g., 140 parts) is added, and the paste is suitable for processing through an extruder. A suitable extruder would be a Kitchen Aid mixer fitted with a pasta extruder and die. The rod prepared from extrusion through a pasta die can then be used as the forming mandrel for a spiral winding machine and a tobacco containing film can be used to form a wrapping around the tobacco core.

Example AO

Compression Molded Cinnamon Flavored Tobacco Stick

TABLE AO1

| Tobacco | 23.84% |
|---|---|
| Starch | 24.09% |
| HPMC | 4.97% |
| Flavor | 15.90% |
| Filler | 19.27% |
| $Na_2CO_3$ | 2.98% |
| Sweetener | 0.99% |
| Plasticizer | 4.97% |
| Water | 3.00% |

The following ingredients were weighed and combined in a container of suitable volume:

MIX1

| HM100PA2208 (Wolff Cellulosics) | 11.16 g |
|---|---|
| B700 (Grain Processing Corporation) | 55.77 g |
| Cinnamon Powder | 24.54 g |
| Fibersol-2 (Matsutani) | 44.61 g |
| $Na_2CO_3$ | 6.69 g |
| Sucralose (Tate & Lyle) | 2.22 g |
| Tobacco Powder (average particle size <80 μm) | 55.77 g |

The resultant mixture was mixed until homogeneous. In a separate container were weighed the following ingredients:

MIX2

| Glycerin | 11.16 g |
|---|---|
| Cinnamon Flavor | 11.16 g |

MIX1 was added to the stainless steel mixing bowl of a Kitchen Aid stand mixer. MIX2 was incorporated slowly to the mixture over a time period of 3 minutes with the aid of a paddle attachment at a medium-low speed. Following this addition, 76.92 g of water was added to the mix in the same manner. The resulting paste was allowed to rest at room temperature for a period of 5 minutes.

Following the rest period, the paste was fed through a ⅛ inch aperture strand forming unit which had previously been attached to the Kitchen Aid mixer. The strands produced were cut to between 1½ and 2 inches in length, and stored in suitable containers.

A set of platens with 2 inch by ¼ inch opposing mold cavities was heated to between 300-330° F. A formed strand was placed in the lower cavity, and the mold was closed by means of a hydraulic press. The mold was allowed to remain closed for a period of 30-60 seconds, providing a means for cooking the starch component of the unit and the release of a portion of the volatile components.

The newly formed stick, measuring approximately 2 inches by ⅛ inch, comprised a smooth rigid outer layer, and a rigid foam-like inner mass. The unit disintegrated in the mouth over a period of 1-2 minutes.

Example AP

Compression Molded Apple Flavored Tobacco Stick

TABLE AP1

| Tobacco | 23.84% |
|---|---|
| Starch | 24.09% |
| HPMC | 4.97% |
| Flavor | 6.45% |
| Filler | 19.27% |
| $Na_2CO_3$ | 2.98% |
| Sweetener | 10.42% |
| Plasticizer | 4.97% |
| Water | 3.00% |

The following ingredients were weighed and combined in a container of suitable volume:

MIX1

| HM100PA2208 (Wolff Cellulosics) | 11.16 g |
|---|---|
| B700 (Grain Processing Corporation) | 55.77 g |
| Sucrose | 22.29 g |
| Fibersol-2 (Matsutani) | 44.61 g |
| $Na_2CO_3$ | 6.69 g |
| Sucralose (Tate & Lyle) | 1.11 g |
| Malic Acid | 2.22 g |
| Tobacco Powder (average particle size <80 μm) | 55.77 g |

The resultant mixture was mixed until homogeneous. In a separate container were weighed the following ingredients:

| MIX2 | |
|---|---|
| Glycerin | 11.16 g |
| Apple Flavor | 12.27 g |

MIX1 was added to the stainless steel mixing bowl of a Kitchen Aid stand mixer. MIX2 was incorporated slowly to the mixture over a time period of 3 minutes with the aid of a paddle attachment at a medium-low speed. Following this addition, 76.95 g of water was added to the mix in the same manner. The resulting paste was allowed to rest at room temperature for a period of 5 minutes.

Following the rest period, the paste was fed through a ⅛ inch aperture strand forming unit which had previously been attached to the Kitchen Aid mixer. The strands produced were cut to between 1½ and 2 inches in length, and stored in suitable containers.

A set of platens with 2 inch by ¼ inch opposing mold cavities was heated to between 300-330° F. A formed strand was placed in the lower cavity, and the mold was closed by means of a hydraulic press. The mold was allowed to remain closed for a period of 30-60 seconds, providing a means for cooking the starch and sugar components of the unit and the release of a portion of the volatile components.

The newly formed stick, measuring approximately 2 inches by ⅛ inch, comprised a rigid outer layer, and a rigid foam-like inner mass. The unit disintegrated in the mouth over a period of 1-2 minutes.

Example AQ

Extruded Tobacco Sticks

TABLE AQ1

| Tobacco | 24.34% |
|---|---|
| Starch | 58.48% |
| $Na_2CO_3$ | 3.17% |
| Plasticizer | 6.34% |
| Sweetener | 0.79% |
| Flavor | 4.88% |
| Water | 2.00% |

The following ingredients were granulated in a manner similar to granulations utilized for tab production, yielding a tobacco granulation with an approximate moisture of 4.50%:

| B700 (Grain Processing Corporation) | 3327.1 g |
|---|---|
| B825 (Grain Processing Corporation) | 120.0 g |
| $Na_2CO_3$ | 181.4 g |
| Sucralose (Tate & Lyle) | 45.4 g |
| Glycerin | 362.9 g |
| Tobacco Powder (average particle size <80 μm) | 1451.5 g |
| Water | 3473.0 g |

The tobacco granulation was introduced to the feed section of a Leistritz Micro-18 Twin Screw Extruder 40:1 L/D, which had been configured for co-rotating extrusion with a medium-shear screw design. Feed rates for the extrusion varied between 1-3 pounds per hour. Barrel zone temperatures varied between 75-100° F. Flavor application rates were established at 5 percent of the process flow; hence cinnamon flavor was incorporated to the process downstream of the granulation feed. Venting of volatiles from the extrusion melt was accomplished by incorporating a venting orifice prior to the discharge die of the extruder.

Solid tobacco sticks, with an approximate diameter of ⅛ inch, were produced by incorporating a strand die at the discharge end of the extruder. Upon discharge, the flexible tobacco strand was cooled to room temperature on an air-cooling conveyor and became rigid, and was cut to approximately 2½ inches in length. The formed tobacco sticks were placed in a suitable container for storage. The stick disintegrated slowly in the mouth over a period of 5-10 minutes.

Gels and Gel Beads.

Compositions of the invention may also be made as gels or gel beads. The composition may contain a soluble or insoluble gel containing tobacco. A gel may be used to encapsulate another material, or another material may encapsulate a gel. Gels may be consumed in hydrated forms containing as much as 70% water. The gels may also be dried resulting in parts containing from 1 to 70% water. The amount of water retained in the gel depends on the properties desired in the finished product. It is possible to prepare tobacco containing gels that provide a wide range of organoleptic characteristics.

Exemplary gel formats for soluble and insoluble gels include kappa carrageenan, sodium alginate, carboxymethyl cellulose, gelatin, pectin, agar, and starches.

Soluble gels containing tobacco can be formed by dissolving the format and at an elevated temperature, e.g., kappa carrageenan at 180° F., and adding the tobacco powder to this solution while continuing vigorous mixing. The hot mixture is then deposited into a mold. Gelatin provides a weak gel at room temperature but firmness and stability can be increased by the addition of agar or starches. Other gelling formats may be used in a similar manner.

Insoluble gels are formed by the addition of a cross-linking agent to a predissolved solution or slurry. The solution is deposited into a mold to form the desired shape and sets up through cooling and/or drying. In most cases, it is necessary to maintain the solution at a high temperature, e.g., greater than 180° F., to prevent premature gelation prior to deposition into the mold. After the gel has set into its final shape, the gel can be packaged as is or be further dried to a desired water content. Cross-linking agents include potassium ions for carrageenan; calcium ions for alginates and low methoxy pectins; and trivalent ions such as aluminum for carboxymethyl cellulose. In insoluble gels (i.e., those that do not orally disintegrate), tobacco organoleptic compounds may leach out of the gel as it is held or chewed in the mouth.

In one embodiment, gel compositions, e.g., beads, have a solid or liquid center. An exemplary solid center includes smokeless tobacco. An interior liquid may be aqueous, non-aqueous, or heterogeneous, depending on the solubility characteristics of the encapsulating bead wall. Aqueous based liquids are typically encapsulated in a water-insoluble gel that can be disrupted, either mechanically or chemically, in the mouth. The encapsulating gel format may include a polymer and a cross linking agent. Exemplary systems include carrageenan and a monovalent cation (e.g. potassium), alginate or pectin and a divalent ion (e.g. calcium), carboxymethyl cellulose and a trivalent ion (e.g. aluminum), and gelatin and gum arabic. The center may or may not include tobacco.

In another embodiment, a water soluble gel encapsulates a non-aqueous filling, e.g., employing ethanol, glycol, vegetable oil, or mineral oil. The water soluble gel and/or the non-aqueous filling may contain tobacco and other ingredients as described herein. Aqueous liquids may also be encapsulated in water soluble gels by the inclusion of additives, e.g., sugars or salts, that sufficiently bind the available water in the filling, thus, preventing the water in the liquid from dissolving the encapsulant. Gel encapsulants also include both hard and soft standard gelatin capsules, which can be filled with liquids or solids.

The center of these gel compositions may or may not include tobacco, e.g., as a tobacco slurry. The gel encapsulant also may or may not include tobacco. An exemplary solid center includes smokeless tobacco. The center may also include a color, sweetener, flavor, or flavor masking agent, which may be the same or different from that of the gel encapsulant. The rate of disintegration for the gel encapsulant and center may also be the same or different. Gels with centers typically have a largest dimension of at most 10 mm, e.g., at most 5 mm. Gel beads with liquid centers may be made by introducing droplets of a tobacco/format mixture into a solution causing gelation of the outer surface of the gel bead and retaining the liquid center. Beads can be formed using commercial processes developed by the Morishita Jintan Company and others and referred to generically as "seamless liquid encapsulation" or "seamless capsule technology." In addition, widely used methods for forming gels of all types including beads have been developed by the suppliers of alginate, carrageenan, and pectin polymers and are well known in the art. The amount of gelation may be controlled, thereby controlling the thickness of the gel encapsulant wall, by varying the concentration of the format, the concentration of the cross-linking agent (e.g., salt), the temperature of the solidifying solution, and the residence time of the gel bead in the solidifying solution. The solution may contain a cross-linking agent or may induce gelation by other means, e.g., a temperature change.

Solid gels may be soluble or insoluble. For solid gels, the tobacco and format, with or without additives, are typically mixed, and the format is allowed to gel. Soluble gels can be obtained by using a self gelling gum, such as gellan gum or kappa carrageenan, or by using a polymer, e.g., gelatin, that sets by a change of temperature. Insoluble solid gels are prepared using a cross linking agent. Such soluble and insoluble gels may be made by introducing droplets into an oil bath, e.g., canola oil, or into an aqueous, cross-linking bath to form a spherical shape. They may also be made to pass through the oil into a water based cross-linking solution. Gels may also be made in molds or may be die cut from sheets.

In another embodiment, a gel composition is supplied as a dry mixture of format, cross-linking agent (e.g., salt), and tobacco, e.g., in powder form, that is solvated by the consumer prior to use. Solvation causes the gel composition to form a solid, which may be placed in the mouth. Typically, the user places the dry mixture of gel ingredients in a mold and adds solvent, which may be aqueous or non-aqueous. The mixture then quickly hydrates, thereby forming a gel which solidifies in the shape of the mold. The solvating liquid may be used to impart flavor or other taste or mouth feel characteristics to the composition. Alternatively, the consumer may place the dry mixture in the mouth for salvation. The solvent may impart flavor or color to the composition.

Gel Examples

Example AR

Gel Beads 100 g of 4% solution of CMC-7MF and 20 g tobacco are combined. Drops are deposited into a 5% solution of water soluble, edible trivalent salt (e.g., $AlCl_3$ or $Al_2(SO_4)_3$). The surface of droplets is then dried with air drying or gentle oven drying.

100 g of 2% kappa carrageenan and tobacco are combined and heated to 180-190° F. Drops are deposited into a cool solution of 5% KCl.

100 g of 4% medium viscosity sodium alginate and tobacco are combined at 150-170° F. Drops are deposited into a cool solution of 5% edible divalent salt (e.g., $CaCl_2$ or Ca citrate).

Beads containing gelatin walls and tobacco slurry centers can be prepared by depositing drops of a cold tobacco slurry (e.g. 60° F.) into a slow moving stream of a dilute, warm gelatin solution (e.g. 130° F.). The warm gelatin coats the outside of the cold droplet and as the gelatin cools and solidifies, it forms a wall of gelatin around the liquid center.

Beads are retrieved from the solution by standard means.

Example AS

Orally Disintegrable Solid Gels

Combine 10 g gelatin and 90 g water and heat to 140° F. to dissolve gelatin. Add 20 g tobacco and pour into a mold. Strength of the gel can be increased by substituting 6 g of gelatin and 4 g of agar and heating to 190° F. to dissolve.

Table AS1 shows exemplary ingredients for fabricating orally disintegrable gels of the invention.

TABLE AS1

|  | Example 1 (parts) | Example 2 (parts) |
| --- | --- | --- |
| Gelatin | 8 | 6 |
| Tobacco | 40 | 40 |
| Flavor | 2 | 2 |
| Insoluble Fiber | 18 | 18 |
| Sweetener | 0.2 | 0.2 |
| Agar | 4 | 6 |
| Soluble Fiber | 15 | 15 |
| Preservative | 0.1 | 0.1 |
| Water | 200 | 200 |

Example AT

Exemplary Insoluble Solid Gels

The following tables and descriptions show exemplary ingredients for fabricating insoluble gels of the invention, i.e., gels that do not orally disintegrate.

TABLE AT1

| Carrageenan Gels | |
| --- | --- |
|  | Parts |
| Kappa Carrageenan | 8 |
| Water | 240 |
| Tobacco | 54 |
| Sweetener | 0.5 |
| Soluble Fiber | 27 |
| KCl | 1.5 |

The composition is cast at 180° F. after adding KCl and mixing thoroughly.

TABLE AT2

Alginate Gels

| | Parts |
|---|---|
| Sodium Alginate | 10 |
| Water | 240 |
| Tobacco | 54 |
| Sweetener | 0.5 |
| Soluble Fiber | 27 |
| $CaCl_2$ | 1 |

The composition is cast after adding $CaCl_2$ at 180° F.

TABLE AT3

Carboxy Methyl Cellulose Gels.

| | Parts |
|---|---|
| CMC-7MF | 10 |
| Water | 240 |
| Tobacco | 54 |
| Sweetener | 0.5 |
| Soluble Fiber | 27 |
| $Al_2(SO_4)_3$ | 1 |

The composition is cast after adding $Al_2(SO_4)_3$ at 180° F.

Example AU

Soluble Gels 416 grams of aqueous 3.9% kappa carrageenan and 51.0 grams of tobacco were combined. The solution was heated to 180° F.-190° F. with stirring, and then the solution was deposited into a mold of the desired shape. Upon cooling, the resultant solid form was removed from the mold and dried to the desired tobacco concentration and gel consistency.

In an alternative process, to a 1000 ml stainless steel container equipped with an overhead mixer, mixing bar and hotplate was added 400 ml of water at greater than 200° F. The water was continuously stirred and heated, and 16.0 g of kappa carrageenan (Gelcarin GP 812, FMC Biopolymer) was added over 2 minutes. The resulting mixture was stirred for an additional 20 minutes, or until all kappa carrageenan was dissolved, then tobacco was added to the homogeneous solution, and the resulting mixture was stirred for an additional 2 minutes while maintaining an optimal temperature of 180° F. To this solution was added 0.8 g powdered Sucralose and 7.0 g cinnamon oil (Wixon Industries) with vigorous stirring. Following an additional 1 minute of stirring, the resulting mixture was quickly transferred via pipette (inner diameter 0.5 cm) to Teflon-coated metal molds to obtain the desired shape. After cooling to room temperature, the resulting gels were removed from the molds and air dried at room temperature for 1 h to several days until the desired consistency of the gels was obtained.

TABLE AU1

Carrageenan Gels

| | Amount parts |
|---|---|
| Kappa Carrageenan | 16 |
| Water | 400 |
| Tobacco | 51 |
| Sweetener | 0.8 |
| Cinnamon Oil | 7.0 |

Example AV

Soluble Gels 100 grams of aqueous 20% gelatin and 33 grams of tobacco were combined. The solution was heated to 140° F.-150° F. with stirring, and then the solution was deposited into a mold of the desired shape. Following refrigeration for a few minutes to a few days depending on desired firmness, the resultant solid form was removed from the mold and dried to the desired tobacco concentration and gel consistency.

In an alternative process, to a 400 ml stainless steel container equipped with an overhead mixer, mixing bar and hotplate was added 80 ml of water at 140° F. The water was continuously stirred and heated, and 20.0 g of Gelatin (Type A 250 Bloom 40 Mesh, Gum Technology) was added over 2 minutes. The resulting solution was stirred for 5 minutes or until the gelatin was dissolved, then 33 g of tobacco was added in portions over 2 minutes. The resulting mixture was stirred for an additional 1 minute, then 0.3 g powdered Sucralose and 1.0 g of oil of peppermint (rectified, Blend SX 0910001, Essex Labs) were added, and the mixture was vigorously stirred for an additional 1 minute while maintaining a temperature of 140° F. The resulting mixture was transferred via pipette (inner diameter 0.5 cm) to Teflon-coated metal molds to obtain the desired shape. After cooling to room temperature, the resulting gels were removed from the molds, and the gelatin was set by refrigeration at 40° F. for 1 hour to several days depending on desired firmness of the finished piece.

TABLE AV1

Gelatin Gels

| | Amount parts |
|---|---|
| Gelatin | 20 |
| Water | 80 |
| Tobacco | 33 |
| Sweetener | 0.3 |
| Peppermint Oil | 1.0 |

Example AW

Gel Beads

A solution of 4% sodium alginate (Keltone LV, International Specialty Products) was prepared by adding 12 g sodium alginate to 288 g of water heated to boiling, followed by stirring and continuous heating of water on a hot plate for 30 minutes or until the solution was homogeneous (stock solution A). A second solution of 0.50 M disodium hydrogen phosphate was prepared by dissolving 33.5 g disodium hydrogen phosphate heptahydrate in 200 ml of water with warming and stirring of the resulting mixture until the salt was dissolved, followed by adjusting the solution to 250 ml with water. To 100 g of aqueous 0.50 M disodium phosphate was added 20 grams of tobacco and the resulting solution was stirred for 5 minutes (stock solution B). To 50 g of the resulting tobacco slurry (stock solution B) was added 50 ml of aqueous 4% sodium alginate (stock solution A), and the resulting mixture was stirred for 5 minutes. To flavor, 0.20 g of powdered Sucralose and 0.80 g of oil of peppermint (rectified, Blend SX 0910001, Essex Labs) were added to the resulting tobacco/sodium alginate slurry (solution C), and the mixture was stirred for 2 minutes.

To prepare gel beads from solution C, a solution of aqueous 5% $CaCl_2$ was prepared by adding 5 g of $CaCl_2$ to 95 g of water with stirring until the calcium chloride was dissolved (solution D). Solution C was then added drop by drop to solution D by pipette from a height of 10 inches. The outer coat of each droplet solidified upon exposure to solution D, forming a solid gel-like outer coat with a liquid center that sank to the bottom of the calcium chloride solution. The gel beads were allowed to remain in the calcium chloride solution for 2-4 minutes, removed, and allowed to air dry for several minutes.

|  | Amount parts |
|---|---|
| Solution A | |
| Sodium alginate | 12 |
| Water | 288 |
| Solution B | |
| Disodium hydrogen phosphate heptahydrate | 13.4 |
| Water | 86 |
| Tobacco | 20 |
| Solution C | |
| Solution A | 50 |
| Solution B | 50 |
| Sucralose | 0.2 |
| Oil of peppermint | 0.8 |
| Solution D | |
| Calcium chloride | 5 |
| Water | 95 |

Consumable Units.

Compositions of the invention may also be fabricated as consumable units. These units may be packaged as edible or inedible materials. In one embodiment, the consumable unit includes tobacco (e.g., smokeless tobacco) or a tobacco composition, e.g., flakes, tabs, beads, granules, or other tobacco composition as described herein, and a wrapping, e.g., a pouch. The wrapping, in one embodiment, may act as an adhesive to hold the composition together, e.g., to hold a plurality of tabs, beads, flakes, etc. together. Alternatively, the wrapping may enclose the composition, e.g., loose tabs, beads, flakes, etc. The composition may also include a liquid, e.g., a tobacco slurry. The wrapping may or may not be orally disintegrable. Orally disintegrable wrappings may be used to enclose aqueous or non-aqueous liquids. When an aqueous liquid is employed with a water soluble wrapping, the liquid includes an agent to prevent dissolution of the wrapping. Exemplary agents include sugars, salts, and other hydrophilic agents capable of binding water sufficiently to reduce water activity to a level at which the water is no longer available to interact with and dissolve the water soluble wrapping. The wrapping may also enclose a moldable tobacco composition that conforms to the mouth or holds its shape in the mouth. In one embodiment, an orally disintegrable wrapping encloses smokeless tobacco, e.g., dry snuff or tobacco, that is perceived as soluble (e.g., less than 80 .mu.m particle size). Orally disintegrable smokeless tobacco compositions may be introduced to consumable portion packs which have been formed on continuous thermoforming or horizontal form/fill/seal equipment or other suitable packaging equipment using edible films (which may or may not contain tobacco) made in accordance with the subject technology. Consumable units may also contain two or more, individually wrapped portions of tobacco, e.g., all contained within a larger package, one containing the other portions, or none of the portions contained with another. When multiple portions are used, any two may have the same or different flavor, color, form of tobacco, or rate of disintegration.

Exemplary wrapping materials include films formed from film compositions based on formats such as HPMC, CMC, pectin, alginates, pullulan, and other commercially viable, edible film forming polymers, such as those described herein. Other wrapping materials may include pre-formed capsules made from gelatin, HPMC, starch/carrageenan, or other commercially available materials. Such wrapping materials may include tobacco as an ingredient. Wrappings which are not orally disintegrable may include woven or nonwoven fabrics; coated or uncoated paper; or of perforated or otherwise porous plastic films. Wrappings may also be colored. Exemplary consumable units include those formed by any method used in commercial packaging, e.g., blister pack and stik-pak (e.g. a small package formed on a vertical form/fill/seal packaging machine).

Consumable Unit Examples

The following description provides exemplary ingredients for fabricating consumable units of the invention.

Example AX

Films or Capsules Encapsulating Beads, Powders, Tabs, etc

Any of the compositions described herein can be encapsulated with a film or capsule. The encapsulant may provide color, stability (e.g., during storage, handling or consumption), or organoleptic properties (e.g., flavor, sweetness, smell, or mouth feel). The encapsulant may also contain tobacco.

A vacuum forming tool is constructed which has a series of cavities which are shaped as circles with diameter of $\frac{3}{4}^{th}$ inch and depth of $3\frac{3}{8}^{th}$ inch. Films as described herein are prepared with and without tobacco as an ingredient. These films are introduced to a vacuum forming machine with a vacuum forming tool. The films are placed over heating elements and warmed to a temperature of 200° F. The films are then quickly placed on the vacuum forming tool, and a vacuum is pulled to draw the film into the cavities. The films are then cooled to set the shapes. Tobacco powder is then introduced into each cavity. A second sheet of film prepared with or without tobacco is selected and coated (by wiping the surface of the film with a wet felt) with a thin layer of water to create a sticky, adhesive surface. The sticky surface is placed on top of the formed sheet wherein each cavity is filled with a tobacco product. The sheets are pressed together to form closed consumable units. Each cavity is then cut out of the vacuum formed sheet to create individual units. A unit is placed in the mouth wherein the film disintegrates and disperses the tobacco in the oral cavity.

Example AY

Tobacco Particles in a Water-Soluble Bag

Smokeless tobacco particles or powder, e.g., snuff, may be placed in a water-disintegrable bag. When placed in the mouth, the bag disintegrates after a specified period of time. The bag may contain a single serving of tobacco. It may also contain additional additives as described herein. The tobacco may also adhere to itself as a moldable plug once the wrapping disintegrates.

The disintegrable bag may be formed using films such as those described herein. The film can be formed into a bag using commercially available packaging equipment such as vertical form/fill/seal machines (e.g. stick pack machines), horizontal form/fill/seal machines, flow wrappers, thermoformers (blister pack machines), and other equipment common to the art.

Example AZ

Tobacco Particles in Film/Fabric Laminations

Smokeless tobacco particles or powder may be placed in a bag that is formed from an open or highly porous wrapping material, e.g., fabrics, paper or plastic films, which has been laminated to a water-soluble wrapping film. The water-soluble film layer provides protection for the tobacco contents and prevents the tobacco from sifting through the openings of the insoluble material during storage and handling. Once the bag is placed in the mouth, the water-soluble film layer dissolves or disintegrates.

Example BA

Film Pouches Containing Tobacco

Films as described herein in Film Examples N, O, P, and Q were used to manufacture tobacco containing pouches. Individual units approximately 1 inch by 1¼ inches were cut from each sheet of manufactured film. The unit was folded over lengthwise and heat-sealed using a Clamco Model 210-8E impulse sealer. One end of the formed unit was also sealed in the same manner. A flavored tobacco granulation was fed to the interior of the formed pouch, and the final seal was made as described to seal the pouch. The tobacco containing pouch disintegrated in the mouth between 20 seconds and 1 minute, releasing the contents of the pouch.

Insoluble Matrices.

Tobacco may also be coated onto or entrapped within an insoluble matrix. Tobacco can be dispersed to form a slurry in an aqueous solution of a format, as when forming a film; this slurry can be coated on to an insoluble matrix or can be used to saturate a porous insoluble matrix. The slurry may then be converted into a soluble or insoluble gel or it may simply be dried to form a coating. When a portion of this coated/saturated insoluble matrix is placed in the mouth, leaching of organoleptic components occurs through dissolution, chewing, or other means. In one embodiment, tobacco in a format is introduced into a porous matrix, e.g., an open. cell polyurethane foam or a high loft polyester nonwoven fabric. The insoluble matrix may be placed wholly in the mouth, or it may be disposed on a stick or other handle, which remains partially outside the mouth during consumption. In another embodiment, tobacco in a format is blended with an incompatible liquid, e.g., a dispersion of carnauba wax in water, deposited in a mold, and quickly cooled to cause a phase separation such that the tobacco slurry is disposed within a waxy structure. These matrices may also be chewable.

Formats for use in retaining the tobacco in the insoluble matrix include any of the film forming polymers described herein; any of the gelling systems described herein and any of the coating materials described herein.

Insoluble Matrix Examples

Example BB

Polyurethane Foam A

A film forming composition which contains finely ground tobacco as described herein is used to saturate a piece (e.g., 12 inches by 12 inches by 1 inch) of open cell polyurethane foam (Stephenson & Lawyer, Inc. Grand Rapids, Mich.). The saturated foam is placed on a metal tray and is put into an air circulating laboratory oven preset at 175° F. for one hour. When the foam is removed from the oven, the tobacco containing composition has dried to form a coating that uniformly covers all the interstices of the polyurethane foam. The coated foam is cut into pieces of a size (e.g., 1 inch by 1 inch by 1 inch) suitable to place in the mouth. After use, the polyurethane foam is removed from the mouth and discarded.

Example BC

Polyurethane Foam B

A sodium alginate and calcium salt gel composition containing finely ground tobacco as described herein is used to saturate an open cell polyurethane foam (e.g., 12 inches by 12 inches by 1 inch). The alginate gel is maintained at a temperature of 180° F. to prevent premature setting of the gel. The hot alginate gel is poured on to the polyurethane foam, which is placed on a metal tray and then quickly cooled in a refrigerator at 40° F. to set the gel. The foam is then placed in a laboratory oven preset at 175° F. for 10 minutes to surface dry the gel and to reduce moisture content to 50% based on dry weight of the gel. The partially dried gel fills voids in the polyurethane foam. The foam is cut into pieces and is placed in the mouth. A further example of gels in an insoluble matrix is obtained by drying the gel to a lower moisture content (e.g., 10% based on dry weight of the gel). The tobacco containing gel exhibits a firm, rubbery texture within the foam matrix and rehydrates slowly when placed in the mouth and chewed. After use, the polyurethane foam is removed from the mouth and discarded.

Hollow Shapes.

As discussed above, films or thin sheets of material may be wrapped, extruded, blow molded, or otherwise shaped to form tubes, straws, or other hollow shapes. Exemplary film or sheet materials are disclosed in the film section herein. Such hollow shapes may be single or multilayer. When multiple layers are used, some may contain tobacco while others may contain colors, flavors, sweeteners, or other compounds as described herein. Different layers may also be employed for stability during handling or to control disintegration during consumption. A spiral wrapped hollow shape, e.g., tube or straw, may require an adhesive (e.g., CMC or guar) to keep from unraveling. The layers in a multilayer hollow shape may contain the same or different color or flavor, and such layers may disintegrate at the same or different rates. As with films, tobacco may also be disposed within one or more layers or may be disposed between layers in a sandwich arrangement. The hollow shape may also include a disintegrant to hasten disintegration.

The compositions described above may be hollow or filled. The filling may include tobacco, a flavor, sweetener, flavor masking agent, or a color. The flavor or color of the filling may be the same or different than the hollow shape. The filling is typically a gel (solid or flowable) but may also be mechanically rigid or may be composed of a powder or other product form. Exemplary filling materials include gels as described herein. A hollow shape may also be filled with a composition that disintegrates more rapidly than the shape, e.g., to provide tobacco at different times based on the rate of disintegration.

In one embodiment, a tobacco core (e.g., formulated with tobacco and a format) can be extruded from a single or twin screw extruder into a coextrusion die. In a separate single or twin screw extruder, a water soluble, thermoplastic outer layer (e.g., formulated with a format and a flavor) can be introduced to the coextrusion die to create a coated rod. A typical thermoplastic outer layer can be provided with a formulation based on hydroxypropyl cellulose (HPC) which is extruded at a temperature between 220-370° F. In addition, a rigid extruded tobacco rod may become a core which is encased in a wrapped film.

In one example, a thermoplastic formulation containing hydroxypropyl cellulose, tobacco, flavor, and sweetener can be blow molded to form a hollow shape.

In another example, films as described herein were additionally used to manufacture spiral-wound straws and/or sticks. Strips of film approximately 10 inches by ¾ inch were cut from each sheet of manufactured film. A strip of paper of equal size was cut and wound spirally around a 3/16 inch diameter stainless steel mandrel. The paper was secured about the mandrel with tape on each end. A strip of film was wound spirally about the paper in the same fashion, overlapping each spiral by 1/16 inch. At each overlap the film strip was glued to itself with a 30% solution of gum arabic. The process was repeated with two additional plies of film. The mandrel and newly formed spiral-wound film straw/stick was placed in a side-swept forced air oven at 75° C. (VWR model 1330FM) for 15 minutes to dry. Upon removal from the oven, the spiral-wound straw/stick was removed from the mandrel, and the paper "core" removed from the interior of the straw/stick. The resultant straw/stick was cut into various sizes.

For example, spiral-wound straw/stick products were prepared using tobacco containing films as described in Example N. Flavored Tobacco Film for Sticks/Wraps/Pouches/Vacuum Forming. Straw/stick products containing one layer, two layers and three layers of Example N films were prepared as described. When placed in the mouth, the straw/stick disintegrated gradually over a period of 1 to 5 minutes.

In another example, straw/stick products were prepared using two layers of film as described in Example N. A third layer of film, prepared as described in Example O. Flavored/Colored Film for Sticks/Wraps/Pouches, was provided on the top or outside of the straw/stick. The film from Example O was red in color, cinnamon flavored and did not contain tobacco. This straw/stick, when placed in the mouth, disintegrated gradually over a period of 1 to 5 minutes In another example, straw/stick products were prepared using three layers of film as described in Example P. Peach Flavored Film for Sticks/Wraps/Pouches. The film from Example P contained tobacco powder and peach puree. The straw/stick was prepared as above. The straw/stick disintegrated gradually over a period of 1 to 5 minutes.

In yet another example, straw/stick products were prepared using three layers of film as described in Example N and Example Q. One layer of tobacco containing film prepared in Example N was used. A second layer of opaque, white film prepared as in Example Q was wound over the first layer of film and offset by $1/8^{th}$ inch. A third layer of tobacco containing film as prepared in Example N was wound over the second layer and again was offset by $1/8^{th}$ inch. The affect was to provide a spiral-wound straw/stick with a striped appearance. The straw/stick, when placed in the mouth, disintegrated gradually over a period of 1 to 5 minutes.

In another example, hollow tobacco straws, with diameters ranging from ⅛ to ¼ inch, were produced by methods similar to those employed in Example AQ of Shaped Parts; however, a tube die was employed in the manufacture of the straw. The straw(s) disintegrated slowly in the mouth over a period of 5-10 minutes. Similar articles may be manufactured with a filling, with methods known in the art (i.e. co-extrusion).

D. Modifications

Any tobacco composition described herein may be modified in various ways. For example, a composition may be coated in single or multiple layers. Such coatings are employed, e.g., for handling, disintegration rate, taste, and color. Exemplary coatings include HPMC. Coatings or decorative patterns may be applied to the surface of the film using processes known in the art, e.g., spraying, brushing, roll coating, doctor bar casting, slot coating, extrusion coating, hot melt deposition, depositing particles or flakes, and other typical methods. Coatings may be matte or glossy. A coating may contain a color, flavor, sweetener, or flavor masking agent, as described herein. The color, flavor, sweetener, or flavor masking agent in the coating may be same or different as the underlying composition. In addition, multiple coatings may also contain the same or different color, flavor, sweetener, or flavor masking agent. The coating may also disintegrate at a different rate than the underlying composition. For example, a coating may disintegrate faster than the underlying composition to provide a burst of flavor or other organoleptic components. An orally disintegrable coating may also be placed on a composition that does not disintegrate orally. A coating that does not disintegrate orally may be placed on a composition that disintegrates orally, and such a coating may be removed, e.g., by chewing. Coatings may also be employed to prevent evaporation of volatile components in a composition and to prevent mechanical maceration of a composition prior to use. A coating may also contain tobacco.

Patterns may also be printed on the surfaces of compositions. Printing patterns also encompasses dusting or sprinkling compounds on the surface of a composition. The pattern may be random or in a design, e.g., a logo. All printing processes known in the art, e.g., offset, flexographic, gravure, ink jet, laser, screen printing, and other typical methods may be used. The printed pattern may or may not contain a color, flavor, sweetener, or flavor masking agent, as described herein. The color, flavor, sweetener, or flavor masking agent in the pattern may be same as or different from the underlying composition. In addition, multiple patterns may also contain the same or different color, flavor, sweetener, or flavor masking agent. The printed pattern may also contain tobacco, e.g., up to 1-99%, preferably 10-50%. Such a pattern may contain more tobacco, percentage-wise or in an absolute sense, than the underlying composition.

Flakes may also be added to compositions described herein. Flakes may be mixed into the composition, may be placed within a void in the composition, or may be placed on the surface, e.g., and adhered by a coating. Flakes may or may not contain a color, flavor, sweetener, or flavor masking agent, as described herein. The color, flavor, sweetener, or flavor masking agent in the flakes may be same or different as the underlying composition. In addition, multiple flakes may also contain the same or different color, flavor, sweetener, or flavor masking agent. Flakes may also contain tobacco, e.g., up to 99%, preferably up to 50%. Flakes may be made by standard film forming technology as described herein. Flakes may contain more tobacco, percentage-wise or in an absolute sense, than the underlying composition.

Once the printed, coated, or decorated film has been prepared, an additional layer of film may be applied to cover, protect and seal the printed, coated or decorated surface.

Compositions of the invention may be shaped in various forms, e.g., plants and geometric shapes (e.g., round, square, rectangular, triangular, oval, octagonal, and the like). In addition, compositions may contain a pattern in relief (positive or negative) on the surface. Such a pattern may be a design, such as a logo.

Composite compositions, i.e., compositions including two or more of the different types of products described herein, are also contemplated by the invention. For example, a shaped part may contain regions of gel compositions, e.g., having a variety of flavors. In another example, a tab may be surrounded by a gel. Composite compositions may also have different rates of disintegration.

E. Packaging

Individual compositions will be packaged as appropriate for the contents of the composition. Preferably, the compositions are stored in a waterproof case and are stable between 40 and 120° F. Compositions are typically dry, flexible, and non-adhesive while in storage. Alternatively, compositions may be packaged using non-stick barriers, e.g., plastic film or paper, between servings. Compositions may also be provided in a bulk form, from which individual servings are separated.

In another embodiment, the package is water impermeable and water insoluble, and tobacco, e.g., in liquid, slurry, or flowable gel form, is disposed within the package, e.g., a squeezable plastic package, a bellows, or a spray bottle, and is capable of being dispensed into the mouth from the package. The bellows may be compressed for oral use. Solutions or slurries are prepared for use in a plastic bellows container or other similar consumer packaging containers wherein the liquid is injected into the mouth by squeezing the package. Thixotropic polymers are combined with tobacco and other ingredients to prepare higher viscosity solutions suitable for use in other containers. Tobacco particles can be of greater size, but must still be small enough to pass through the orifice of the container. For spray bottles, a stable tobacco slurry is contained in the bottle; tobacco particles are sized to be able to pass through a spray nozzle without blocking the orifice; and the tobacco slurry is sprayed directly in the oral cavity. Liquid sprays are prepared by dissolving a thixotropic polymer such as xanthan, gellan or dextran in water and suspending tobacco particles in a low viscosity (e.g., <50 centipoise) solution. Other compounds, such as flavor, sweetener and dispersant, can be added to the solution. The tobacco particles are ground to a particle size (e.g., <80 microns) to permit the homogeneous solution to pass through the orifice of a spray bottle. Other packages may be otherwise squeezed or used to expel the tobacco into the oral cavity.

F. Solutions

The following tobacco solutions may be included in any composition described herein.

Example BD

Sprayable Solution

A solution is prepared by mixing 0.2 grams of xanthan (Kelzan from C. P. Kelco) in 78.6 grams of cool water with vigorous mixing for 30 minutes. To this solution is added 20 grams of finely ground tobacco, 0.2 grams of sucralose, and 2 grams of cinnamon flavor while continuing to mix vigorously. The solution viscosity is adjusted with water to a viscosity of 50 centipoise.

Example BE

Thick Solution

A solution is prepared by mixing 1 gram of xanthan (Kelzan from C. P. Kelco) with 76.8 grams of cool water while mixing vigorously for 30 minutes. To this is added 20 grams of fine tobacco, 0.2 grams of sucralose and 2 grams of cinnamon flavor while continuing to mix vigorously. Solution viscosity is 1,500 centipoise.

Example BF

Paste

A paste is prepared by adding 2 grams of a medium viscosity carboxymethyl cellulose (CMC 7MF from Hercules, Inc.) to a mixture of 35.8 grams of cool water and 40 grams of glycerine with vigorous mixing for 30 minutes. To this mixture is added 20 grams of fine tobacco powder, 0.2 grams of sucralose, and 2 grams of cinnamon flavor. A thick paste is prepared which is highly shear sensitive. This paste can be introduced to a tube or other squeezable package where the shear force from squeezing reduces the viscosity to permit flow of the paste.

Other Embodiments

The description of the specific embodiments of the invention is presented for the purposes of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference.

Other embodiments are within the claims.

What is claimed is:

1. An orally disintegrable smokeless tobacco product comprising;
   between 20% and 45% of a water-soluble polymer on a dry weigh basis;
   between 1% and 40% of tobacco having an average particle size of 250 µm or less on a dry weigh basis; and
   between 2% and 5% of one or more sweeteners on a dry weigh basis,
   wherein said product is in the shape of a stick or a tab.

2. The product of claim 1, wherein said tobacco has an average particle size of 80 µm or less.

3. The product of claim 1, said tobacco having an average particle size of 75 µm or less.

4. The product of claim 1, said tobacco having an average particle size of 50 µm or less.

5. The product of claim 1, said tobacco having an average particle size of 25 µm or less.

6. The product of claim 1, wherein said product has a length that is not longer than 6 inches.

7. The product of claim 6, wherein said product has a length that is not longer than 2.5 inches.

8. The product of claim 1, wherein said product has a diameter of about ⅛ inches.

9. The product of claim 1, wherein said product has a disintegration time of about 1 to about 60 minutes.

10. The product of claim 1, wherein said product has a disintegration time of about 1 minute or less.

11. An orally disintegrable smokeless tobacco product comprising:
   between 5% and 80% of a water-soluble polymer;
   tobacco having an average particle size of 250 μm or less, said product comprising about 1% to about 40% tobacco on a dry weight basis; and
   one or more sweeteners,
   wherein said product is in the shape of a stick or a tab.

12. An orally disintegrable smokeless tobacco product comprising:
   between 5% and 80% of a water-soluble polymer;
   tobacco having an average particle size of 250 μm or less, said product comprising about 20% to about 40% tobacco on a dry weight basis; and
   one or more sweeteners,
   wherein said product is in the shape of a stick or a tab.

13. The product of claim 1, wherein the sweetener is selected from the group consisting of sucrose, sucralose, acesulfame potassium, aspartame, saccharine, cyclamates, lactose, glucose, fructose, sorbitol, and mannitol.

14. The product of claim 1, further comprising between 0.5% and 4.0% of one or more flavor oils.

15. The product of claim 1, further comprising between maltodextrin in an amount of less than 50%.

16. The product of claim 1, further comprising between 0.1% and 15% disintegrant.

17. The product of claim 1, further comprising between 0.1% and 5.0% emulsifier.

18. The product of claim 1, wherein the product further comprises sodium carbonate.

19. An orally disintegrable smokeless tobacco product comprising:
   between 10% and 20% starch on a dry weight basis;
   between 20% and 45% of a water-soluble polymer on a dry weight basis; and
   between 1% and 40% of tobacco on a dry weight basis, the tobacco having an average particle size of 250 μm or less;
   wherein said product is in the shape of a stick or a tab.

20. The product of claim 19, further comprising 0.05% and 4.0% artificial sweetener.

21. The product of claim 19, further comprising 1% and 80% sugar.

* * * * *

UNITED STATES PATENT AND TRADEMARK OFFICE
CERTIFICATE OF CORRECTION

| | | |
|---|---|---|
| PATENT NO. | : 8,636,011 B2 | Page 1 of 1 |
| APPLICATION NO. | : 12/345012 | |
| DATED | : January 28, 2014 | |
| INVENTOR(S) | : James Arthur Strickland et al. | |

It is certified that error appears in the above-identified patent and that said Letters Patent is hereby corrected as shown below:

ON THE TITLE PAGE

Page 4, Column 2, Line 41 (Other Publications), Delete "Vaporette" and insert -- Vaporetto --, therefor.

Page 5, Column 1, Line 17 (Other Publications), Delete "Georga" and insert -- Georgia --, therefor.

Signed and Sealed this
Sixteenth Day of February, 2016

Michelle K. Lee
*Director of the United States Patent and Trademark Office*